United States Patent
He et al.

(10) Patent No.: US 9,411,033 B2
(45) Date of Patent: Aug. 9, 2016

(54) METHODS AND APPARATUS FOR IMAGING WITH MAGNETIC INDUCTION

(75) Inventors: Bin He, Arden Hills, MN (US); Yuan Xu, Falcon Heights, MN (US); Xu Li, Weymouth, MA (US)

(73) Assignee: REGENTS OF THE UNIVERSITY OF MINNESOTA, St. Paul, MN (US)

(*) Notice: Subject to any disclaimer, the term of this patent is extended or adjusted under 35 U.S.C. 154(b) by 1675 days.

(21) Appl. No.: 11/913,894

(22) PCT Filed: May 10, 2006

(86) PCT No.: PCT/US2006/018207
§ 371 (c)(1),
(2), (4) Date: Aug. 6, 2008

(87) PCT Pub. No.: WO2006/122232
PCT Pub. Date: Nov. 16, 2006

(65) Prior Publication Data
US 2009/0018432 A1 Jan. 15, 2009

Related U.S. Application Data

(60) Provisional application No. 60/680,095, filed on May 11, 2005, provisional application No. 60/680,092, filed on May 11, 2005.

(51) Int. Cl.
*A61B 5/05* (2006.01)
*G01R 33/48* (2006.01)
*A61B 5/00* (2006.01)
*A61B 8/00* (2006.01)

(52) U.S. Cl.
CPC .......... *G01R 33/4808* (2013.01); *A61B 5/0093* (2013.01); *A61B 8/00* (2013.01)

(58) Field of Classification Search
CPC ..... A61B 5/0093; A61B 8/00; G01R 33/4808
USPC ............................ 600/437, 547, 558; 73/579
See application file for complete search history.

(56) References Cited

U.S. PATENT DOCUMENTS

| | | | | |
|---|---|---|---|---|
| 4,122,495 A * | 10/1978 | Defranould et al. | .......... | 348/198 |
| 4,296,486 A * | 10/1981 | Vasile | .......... | 367/140 |
| 5,280,011 A * | 1/1994 | Kraitsberg | .......... | C04B 35/45 |
| | | | | 264/427 |
| 6,121,774 A * | 9/2000 | Sun et al. | .......... | 324/303 |
| 6,132,380 A * | 10/2000 | Cohen et al. | .......... | 600/481 |
| 6,520,911 B1 * | 2/2003 | Wen | .......... | 600/437 |
| 6,535,625 B1 | 3/2003 | Chang et al. | | |
| 6,640,635 B2 * | 11/2003 | Nakatsuka | .......... | 73/643 |
| 6,962,082 B2 * | 11/2005 | Hashimoto et al. | .......... | 73/579 |
| 6,974,415 B2 | 12/2005 | Cerwin et al. | | |
| 7,505,811 B2 * | 3/2009 | Hashimshony | .......... | 600/547 |
| 7,648,844 B2 * | 1/2010 | Srivastava et al. | .......... | 436/526 |

(Continued)

*Primary Examiner* — Baisakhi Roy
(74) *Attorney, Agent, or Firm* — Quarles & Brady, LLP

(57) ABSTRACT

An apparatus includes a magnetic energy source to provide a magnetic signal and a detector to detect an acoustic energy signal from a sample stimulated by the magnetic energy signal. A method includes applying a magnetic signal to a biological sample, detecting an acoustic signal from the sample, and processing the acoustic signal to determine the electrical impedance distribution of the sample, and identify disease in the biological sample. A method includes applying a magnetic signal to a sample, detecting a magnetic or electrical signal within the sample, and processing the magnetic or electrical signal to reconstruct electrical impedance distribution of the sample.

17 Claims, 18 Drawing Sheets

(56) References Cited

U.S. PATENT DOCUMENTS

| | | | |
|---|---|---|---|
| 2002/0079891 A1* | 6/2002 | Blumich | G01N 24/08 324/307 |
| 2003/0016010 A1 | 1/2003 | Kandori et al. | |
| 2003/0133596 A1* | 7/2003 | Brooks | 382/115 |
| 2003/0164765 A1* | 9/2003 | Sumi et al. | 340/551 |
| 2003/0190412 A1* | 10/2003 | Koike et al. | 427/180 |
| 2004/0025593 A1* | 2/2004 | Hashimoto et al. | 73/643 |
| 2004/0039298 A1* | 2/2004 | Abreu | 600/558 |
| 2004/0089812 A1* | 5/2004 | Favro et al. | 250/341.6 |
| 2004/0221652 A1* | 11/2004 | Flora et al. | 73/578 |
| 2004/0236217 A1 | 11/2004 | Cerwin et al. | |
| 2004/0247145 A1* | 12/2004 | Luo | H04R 25/43 381/312 |
| 2005/0025797 A1* | 2/2005 | Wang | A61L 31/16 424/422 |
| 2005/0151083 A1* | 7/2005 | Favro et al. | 250/341.6 |
| 2006/0069425 A1* | 3/2006 | Hillis et al. | 623/1.16 |
| 2007/0045544 A1* | 3/2007 | Favro et al. | 250/341.6 |
| 2009/0199577 A1* | 8/2009 | Owada | A23L 3/32 62/66 |
| 2011/0096002 A1* | 4/2011 | Koh et al. | 345/173 |

* cited by examiner

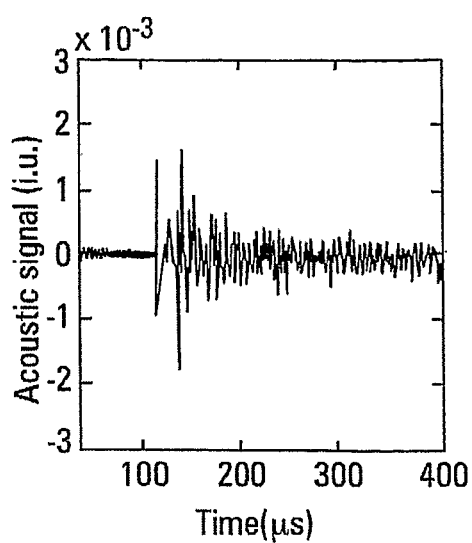
Fig. 9
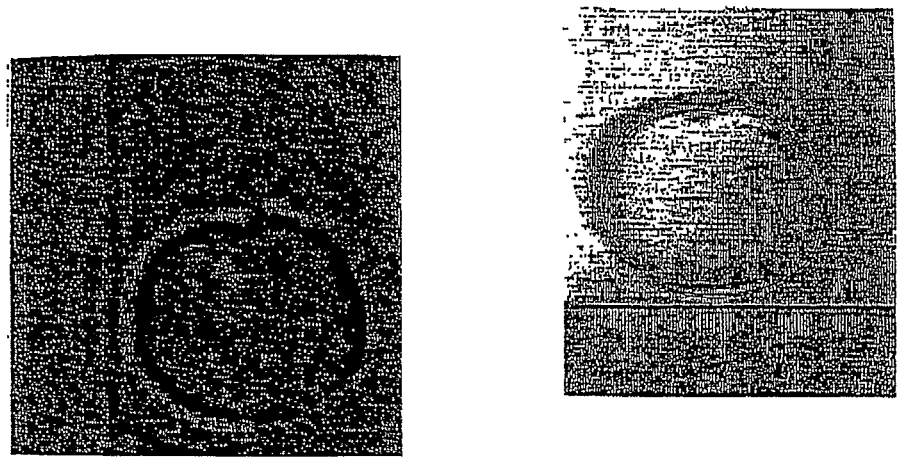
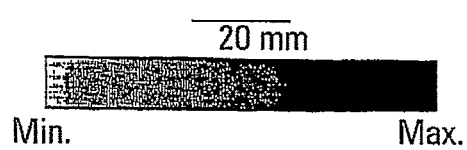
Fig. 10B
Fig. 10A

METHODS AND APPARATUS FOR IMAGING WITH MAGNETIC INDUCTION

CLAIM OF PRIORITY

This application claims priority under 35 U.S.C. §119(e) from U.S. Provisional Application Ser. No. 60/680,092 filed May 11, 2005 and U.S. Provisional Application Ser. No. 60/680,095 filed May 11, 2005. U.S. Provisional Application Ser. No. 60/680,092 and U.S. Provisional Application Ser. No. 60/680,095 are hereby incorporated by reference in their entirety.

STATEMENT REGARDING FEDERALLY SPONSORED RESEARCH

This invention was made with government support under R01-EB000178 awarded by the National Institutes of Health and BES-0411480 and BES-0411898 awarded by the National Science Foundation. The government has certain rights in the invention.

FIELD OF THE INVENTION

The subject mater of the present invention relates to determining physical properties of an object. More particularly, some of the subject matter relates to determining physical and physiological properties of biological tissues in a biological system.

BACKGROUND

Electrical Impedance Tomography (EIT) is an imaging modality that estimates the electrical impedance in the interior of an object from voltage measurements made on its surface by injecting currents via surface electrodes (Barber and Seagar, 1987; Metheral et al., 1996). However, the accuracy and spatial resolution of EIT are currently limited because the boundary voltage measurements are not sensitive to the change in conductivity within the body.

In magnetoacoustic tomography (MAT) (Towe & Islam, 1988; Islam & Towe, 1988; Roth et al., 1994) and the reverse mode—Hall effect imaging (HEI) (Wen et al., 1998), the sample is located in a static magnetic field and current is injected into a sample by applying electrodes on the surface of the sample, and acoustic signals are collected around the object. However, there has been no report on quantitative image reconstruction of electrical impedance.

Magnetic Resonance Electrical Impedance Tomography (MREIT) integrates Current Density Imaging (CDI) (Joy et al., 1989; Scott et al., 1991) and EIT (Barber and Seagar, 1987; Metheral et al., 1996). In MREIT (Woo et al., 1994; Kwon et al., 2002; Gao et al., 2005), a low frequency current is injected into a body through pairs of surface electrodes, and the distribution of the induced magnetic flux density inside the body is measured by a magnetic resonance imaging (MRI) system. The current density distribution inside the body can be obtained using Ampere's law. The body's conductivity distribution can be calculated from the relationship between conductivity and current density. MREIT has been pursued by injecting electrical currents using surface electrodes, with subject being placed within the MRI scanner. The magnetic flux density is measured which is then used to construct current density or impedance distribution within the body. Disadvantages of this method include contact with a patient, pain from current injection, errors caused by incorrectly positioning electrodes, and difficulty injecting currents into the brain due to the low conductivity of the human skull.

SUMMARY OF CERTAIN EMBODIMENTS OF THE INVENTION

Methods and systems have been developed to image distribution of physical properties within an object with magnetic induction. In particular such physical properties include electrical impedance properties.

To provide high spatial resolution of impedance information, methods and systems of magnetoacoustic tomography with magnetic induction (MAT-MI) have been developed. Embodiments combine ultrasound and magnetism. In some embodiments of the invention, a sample is placed in a static magnetic field and a time-varying magnetic field. The time-varying magnetic field induces eddy currents in the sample. The sample emits ultrasonic waves through the Lorenz forces produced by the combination of the eddy current and the static magnetic field. The acoustic waves are sensed by detectors located around the sample, and processed to reconstruct images of the sample, which contain information with regard to electrical impedance. MAT-MI images exhibit the contrast of electrical impedance imaging and the spatial resolution of ultrasound.

In another embodiment of the invention, a sample is placed in a static magnetic field and a time-varying magnetic field. The time-varying magnetic field induces eddy currents in the sample. The sample emits ultrasonic waves and exhibits mechanical force distribution through the Lorenz forces produced by the combination of the eddy current and the static magnetic field. The acoustic waves are sensed by detectors located around the sample, and processed to reconstruct images of the sample, which contain information with regard to mechanical properties distribution within the sample.

In one embodiment of the invention, the acoustic waves are detected by an array of detectors either simultaneously or sequentially during the period the detector array is rotating surrounding the object.

In another embodiment of the invention, the object is placed into an MRI system which exhibits a static magnetic field and also can produce a time-varying magnetic field. The acoustic signals can be sensed by an array of acoustic sensors surrounding the object, which are incorporated into such an MRI system.

In one embodiment of the invention, magnetic induction is used to introduce phase perturbation in the MRI measurements, which can then be used to reconstruct the electrical impedance distribution, by minimizing the difference between the sensed magnetic flux density distribution within the object and a computer-model-generated magnetic flux density distribution within the object.

In another embodiment of the invention, magnetic induction is used to introduce phase perturbation in the MRI measurements, which can be used to compute current density distributions within the object, and then electrical impedance distributions are estimated by minimizing the difference between the measurement derived current density distribution within the object and a computer-model-generated current density distribution within the object.

The use of magnetic induction instead of electrical current injection has the benefits of not requiring contact with the subject, accurate determination of stimulator locations, among others. The magnetic induction can be achieved by using pairs of coils through which current pulses are flowing. Some embodiments may be referred to as Magnetic Resonance Electrical Impedance Tomography with Magnetic Induction (MREIT-MI) for the sake of simplicity.

The present invention can be applied to detect tumors and cancers, such as breast cancers, brain tumors, strokes, infarction, and ischemia. Further, the impedance imaging aspects of the present invention can be used to aid accurate source imaging and localization in the brain and heart, which may aid surgical planning in the treatment of epilepsy or other neurological disorders, brain tumors, and guiding catheter ablation of cardiac arrhythmia.

Some embodiments image materials, such as biological tissue, by injecting external energy onto the material and recording induced signals from the material, and reconstructing images from the signals. In some embodiments, physical activities are induced within a material by using magnetic stimulation, or magnetic induction mechanisms, and measuring acoustic signals. In some embodiments, acoustic energy is injected and magnetic signals are detected.

According to one embodiment, material, such as tissue, is located in a static magnetic field and a pulsed magnetic field. The pulsed magnetic field induces eddy currents in the material. The material emits waves, such as ultrasonic waves, according to the fundamental physics. The signals, for example, acoustic signals, are detected and processed to reconstruct images related to the distributions of the electrical properties such as electrical impedance or currents, or mechanical properties, within the material.

BRIEF DESCRIPTION OF THE DRAWINGS

FIG. 9 is an illustration of a signal that results from wire scattering.

FIGS. 10(a) and 10(b) illustrate an image of a wire loop and the wire loop, respectively.

DETAILED DESCRIPTION OF THE INVENTION

Magnetoacoustic Tomography with Magnetic Induction (MAT-MI)

Apparatus of MAT-MI

Figure 1A:
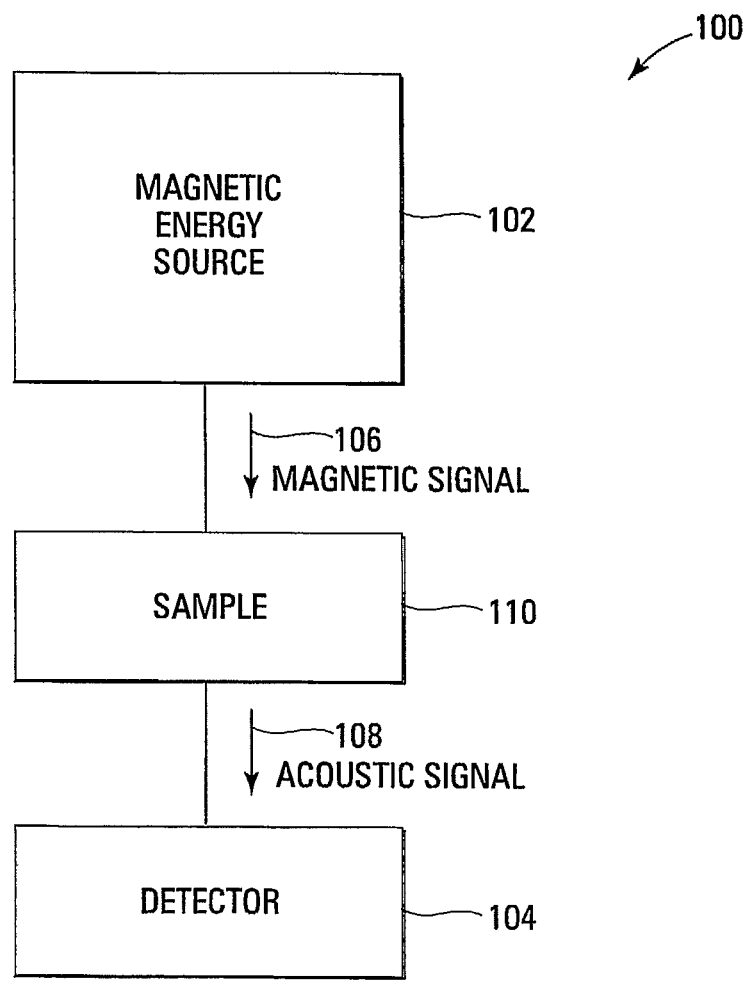
FIG. 1(a) is an illustration of an apparatus including a magnetic energy source and a detector in accordance with some embodiments.

FIG. 1(a) is an illustration of an apparatus 100 including a magnetic energy source 102 and a detector 104 in accordance with some embodiments. The magnetic energy source 102 provides a magnetic signal 106. The detector 104 detects an acoustic signal 108. In operation, the magnetic energy source 102 provides the magnetic signal 106 to stimulate a sample 110. The detector 104 detects the acoustic energy signal 108 from the sample 110. In some embodiments, the magnetic signal 106 includes a static magnetic signal and a non-static magnetic signal. A static magnet signal does not vary with time. A non-static magnetic signal varies with time. In some embodiments, the non-static magnetic signal includes a pulsed magnetic signal. A pulsed magnetic signal includes transitions that are substantially step transitions. A transition is substantially a step transition if the derivative of the transition is substantially infinite. In some embodiments, the sample 110 includes biological material. Exemplary biological materials suitable for use in connection with the apparatus 100 include animal and plant tissue. In some embodiments, the sample 110 includes human tissue. Exemplary human tissue suitable for use in connection with the apparatus 100 includes both living human tissue and dead human tissue. In some embodiments, the sample 110 includes intact biological systems. Exemplary intact biological systems suitable for use in connection with the apparatus 100 includes intact human and intact animal. In some embodiments, the sample 110 includes non-biological material. Exemplary non-biological material includes chemical solutions and solid materials.

Figure 1B:
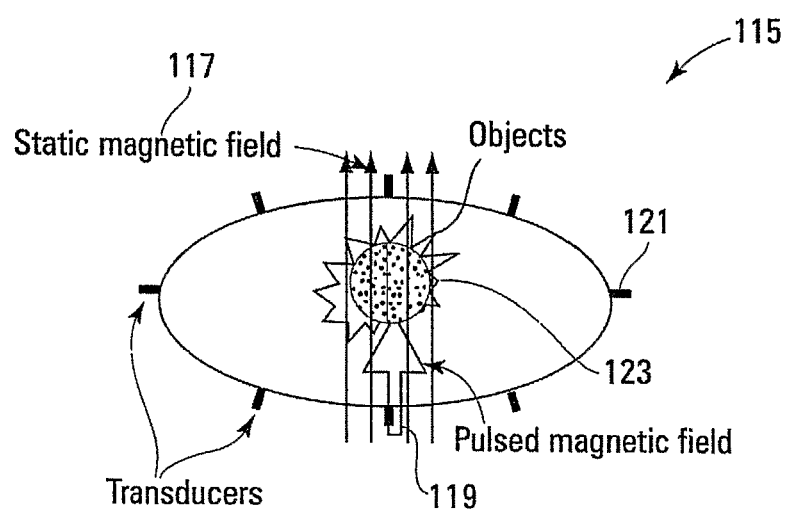
FIG. 1(b) is an illustration of an apparatus including a magnetic filed, a pulsed magnetic field, a transducer, and an object to be imaged in accordance with some embodiments.

FIG. 1(b) is an illustration of an apparatus 115 including a magnetic field 117, a pulsed magnetic field 119, transducers 121, and an object 123 to be imaged in accordance with some embodiments. In some embodiments, the magnetic field 117 is a static, substantially non-changing, magnetic field produced by a permanent magnetic or an electromagnet. The pulsed magnetic field 119 is a magnetic field that changes with time. The pulsed magnetic field can be produced by a changing current in an electromagnet. In some embodiments, the transducers 121 are devices that convert energy from one form to another and detect waves. In some embodiments, the waves are ultrasonic or acoustic waves and the transducers 121 covert the wave energy to electrical energy. In some embodiments, the transducers 121 include or are coupled to focusing elements that concentrate or with focusing sensitivity to waves originated from certain regions of the object 123. The apparatus 115 is not limited to use with a particular number of transducers 121. One or more transducers 121 are suitable for use in connection with the apparatus 115. The apparatus 115 is not limited to use with transducers 121 located over a plane. Transducers 121 can be located over a 3-dimensional surface for use in connection with the apparatus 115. The apparatus 115 is not limited to use for data collection instantaneously with transducers 121. Waves can be recorded by transducers 121 for a certain period of time, and recorded by multiple times, over different periods of time by the transducers 121 after moving transducers 121 to different locations in space, such as by rotating surrounding the object sequentially. The apparatus 115 is not limited to imaging a particular type of object. In some embodiments, the object 121 includes a biological sample, such as biological tissue or a living human. In some embodiments, the object 121 is a material sample such as a semiconductor. In other embodiments, the object 121 is an integrated circuit including first level metalization that is imaged by the apparatus 115.

Figure 2:
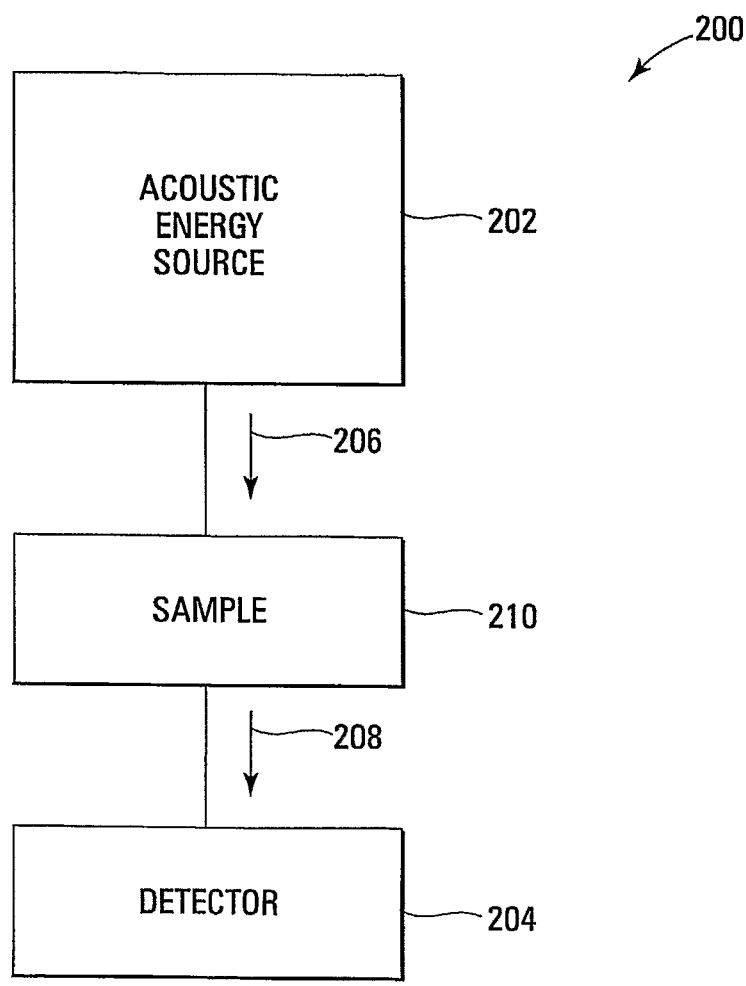
FIG. 2 is an illustration of an apparatus including an acoustic energy source and a detector in accordance with some embodiments.

FIG. 2 is an illustration of an apparatus 200 including an acoustic energy source 202 and a detector 204 in accordance with some embodiments. The acoustic energy source 202 provides an acoustic signal 206. The detector 204 detects a magnetic signal 208 from a sample 210. In operation, the acoustic energy source 202 provides the acoustic signal 206 to the sample 210. The detector 204 receives the magnetic signal 208 from the sample 210. In some embodiments, the sample 210 includes biological material. Exemplary biological materials suitable for use in connection with the apparatus 200 include animal and plant tissue. In some embodiments, the sample 210 includes human tissue, such as living and dead human tissue. In some embodiments, the sample 210 includes intact biological systems. Exemplary intact biological systems suitable for use in connection with the apparatus 200 includes intact human and intact animal. In some embodiments, the sample 210 includes non-biological material. Exemplary non-biological material includes chemical solutions and solid materials, such as semiconductors.

Exemplary 2-D MAT-MI System

Figure 3:
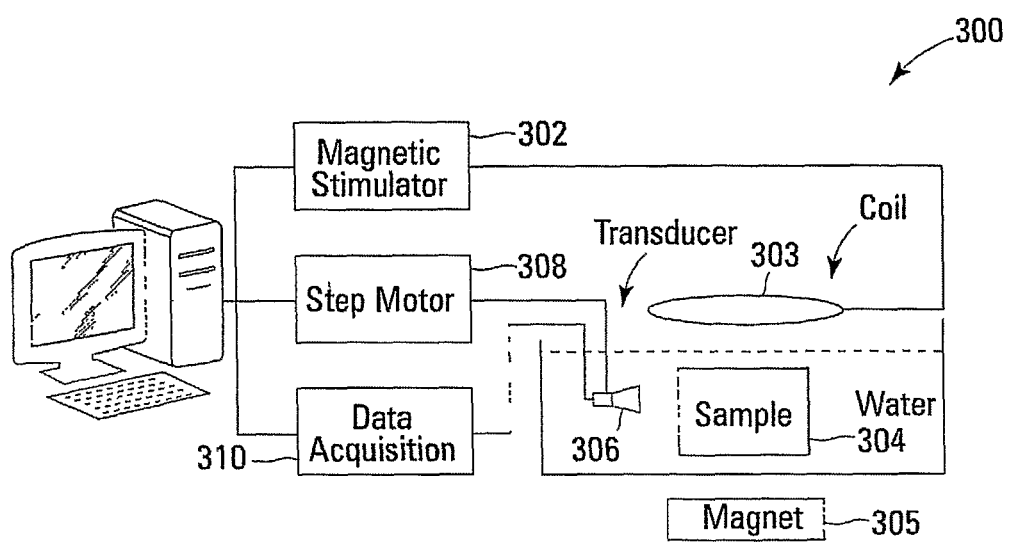
FIG. 3 is an illustration of an experimental setup suitable for use in magnetic acoustic tomography with magnetic induction in accordance with some embodiments.

FIG. 3 is an illustration of an experimental setup 300 suitable for use in magnetic acoustic tomography with magnetic induction in accordance with some embodiments. A magnetic stimulator 302 can send pulsed stimulation (μs) through a coil 303 in a distance from a sample 304 in a magnetic field generated by the magnet 305. An ultrasound sensor 306 driven by a step motor 308 can scan around the sample 304 in an orbit, such as a circular orbit. Data acquisition at the data acquisition module 310 is synchronized with the magnetic stimulation. This composes a 2-dimensional (2-D) MAT-MI system. Because some reconstruction algorithms are intrinsic 3-dimensional (3-D) and require acoustic measurement on a surface surrounding the sample to quantitatively reconstruct the conductivity distribution, this 2-D system provides a simplified means of collecting the acoustic signals. However, it's demonstrated that this 2-D system can still reconstruct the conductivity boundaries of the sample in the scanning cross section. The reconstruction algorithm thus can be simplified to (1)

$$I(r) = -\sum_{i=1}^{N} \frac{r_i \cdot (r_i - r)}{|r - r_i|^2} \tilde{p}(r_i, |r - r_i|/c_s) \quad (1)$$

where $r_i$ is the position of the sensor at the i-th scanning point, $\tilde{p}$ is the pressure signal after filtering.

In the experiment setup 300, the pulse width of the stimulation can be 0.5 μs. Other pulse width may also be used. The radius of the coil is 40 mm. A permanent magnet (50 mm by 50 mm by 25 mm) is placed 2 cm under the sample and creates a magnetic field about 0.1 T along the z-axis at 2 cm from its surface. The transducer (TC3029, Reson Inc.) has a central frequency of 500 KHz. The transducer signal is amplified by 80 dB and sampled at 5 MHz. Because of the limited signal-to-noise ratio (SNR), time averaging was used.

Figure 4:
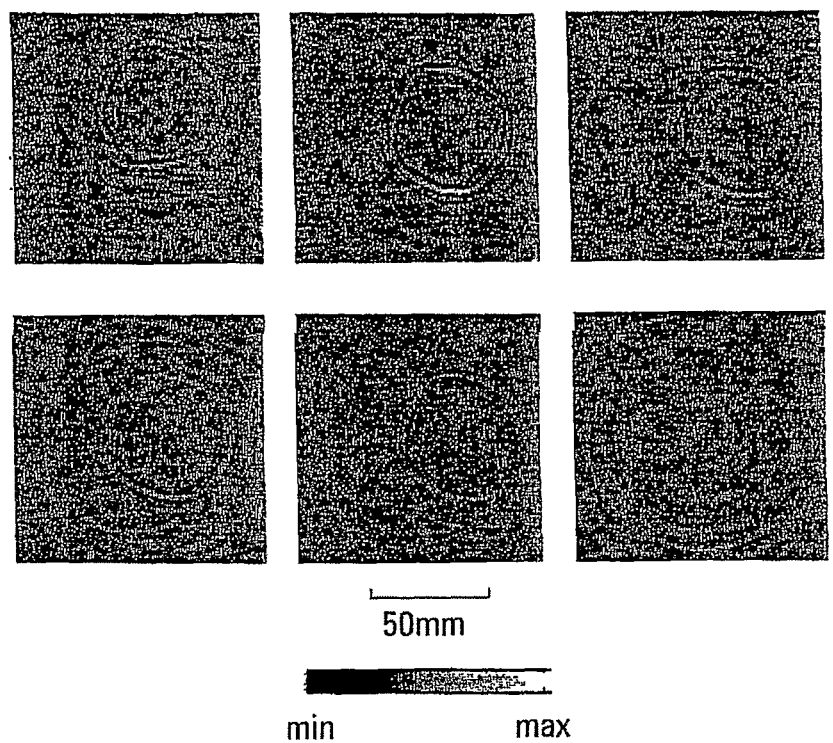
FIG. 4 is an illustration of reconstructed images of saline samples having different salinities produced in accordance with some embodiments.

FIG. 4 is an illustration of reconstructed images of saline samples having different salinities produced in accordance with some embodiments. The image center is the origin of the scanning circle orbit. The saline samples are put in a plastic cup and emerged in water. This creates a conductivity step which is analog to a homogeneous tissue with higher conductivity embedded in a low conductive one. The transducer scans the sample with a 2.5 degrees step. The right bottom image in FIG. 4 (water sample) indicates that the plastic cup has little influence on the reconstructed image. It is shown that this system can distinguish the conductivity difference between water and saline sample with salinity of 1%. In addition, the image boundary intensity positively correlated with the salinity, thus the conductivity contrast of the sample and background.

Figure 5:
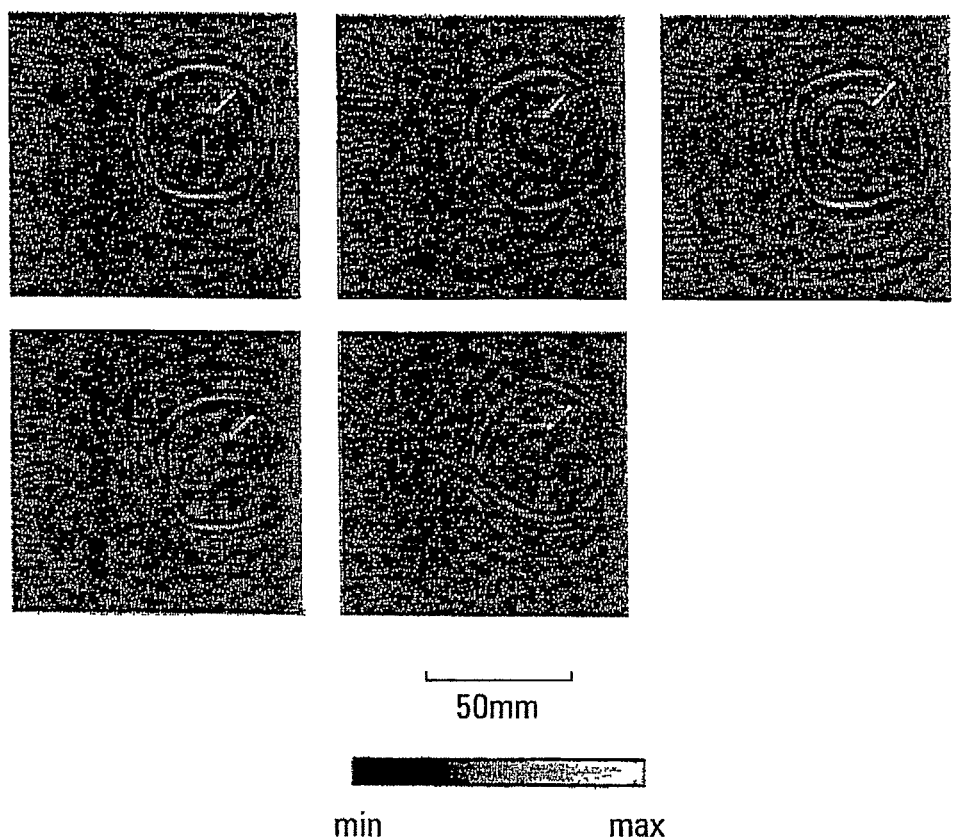
FIG. 5 is an illustration of reconstructed images of double layer gel phantoms with different inner layer sizes and shapes produced in accordance with some embodiments.

FIG. 5 is an illustration of reconstructed images of double layer gel phantoms with different inner layer sizes and shapes produced in accordance with some embodiments. The salinity is 10% for the outer layer and 0% for the inner layer. Plastic film was inserted between the inner layer and outer layer gel to prevent diffusion. The transducer's scanning step is 2.5 degrees. It is shown in FIG. 5 that the shape and size of the conductivity boundaries in the obtained images are consistent with the real sample.

Figure 6A:
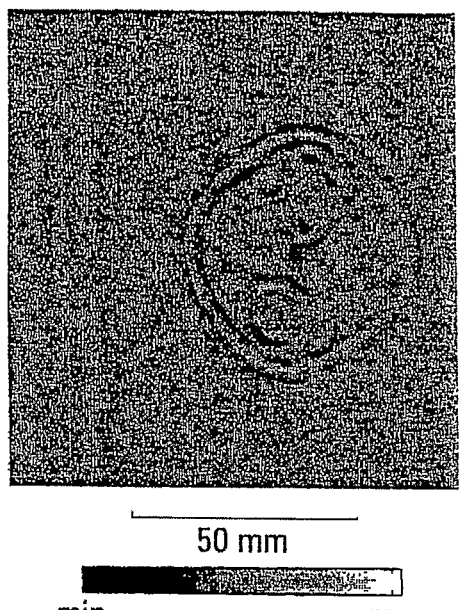
FIG. 6 is an illustration of a reconstructed image of a gel phantom produced in accordance with some embodiments.
Figure 6B:
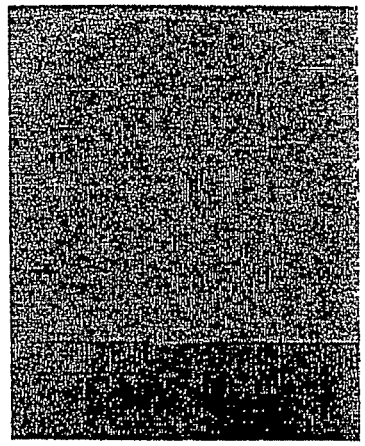
Figure 6C:
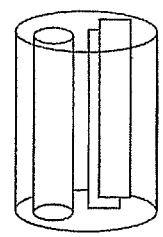

FIG. 6 is an illustration of a reconstructed image of a gel phantom produced in accordance with some embodiments. Two columns of gels (a cylinder shape and a square prism shape) with 0% salinity are embedded in gel of 10% salinity with plastic film inserted. The scanning step is 1.25 degrees. As seen in FIG. 6, the 2-D MAT-MI image is consistent with the cross section of the phantom in terms of shape and size of the conductivity boundary. In addition, more scanning steps in this case led to a better quality image with less backprojection artifacts.

From the current results, it is shown that the width of all the conductivity boundaries in the reconstructed image extends to about 3 mm, indicating an "effective" spatial resolution of 3 mm. Here the spatial resolution is defined as the diameter of the smallest structure that can be reconstructed using the current 2-D MAT-MI setup. This is partly demonstrated in FIG. 6 in that the shortest distance between the inner square prism boundary and the outer layer boundary is 4 mm, which is seen in the reconstructed image. Higher spatial resolution may be obtained by increasing the transducer central frequency and measurement SNR.

The present experiment results from imaging the saline and gel phantoms, which have close conductivity values to those of biological tissue and demonstrate the feasibility and performance of MAT-MI approach to image electrical impedance of biological tissue with high spatial resolution In summary, the MAT-MI approach is demonstrated through a phantom experiment study using the current 2-D system. Conductivity boundary images with high spatial resolution have been obtained from saline and gel.

Methods of MAT-MI

Methods have been developed to estimate current density and electrical impedance of tissue from acoustic measurements. The forward problem and the inverse problem of this method are described below. The formulas for the forward problem can express the acoustic pressure in terms of the eddy current and the static magnetic field. The pressure induced in biological tissue can be determined by computing the acoustic waves from a sphere in a uniform electrical and magnetic field. The formulas for the inverse problem in MAT-MI are also provided.

A. Forward Problem of MAT-MI

In a medium with a current distribution $\tilde{J}$ (in this document, the tilt over a variable means that the variable is a function of time; otherwise, the variable is not a function of time if not denoted explicitly) in a static magnetic field $B_0$, we have the following wave equation for the induced pressure $\tilde{p}(r,t)$ (Roth et al 1994), $$\nabla^2 \tilde{p} - \frac{1}{c_s^2} \frac{\partial^2 \tilde{p}}{\partial t^2} = \nabla \cdot (\tilde{J} \times B_0), \qquad (2)$$

$$\text{where } c_s = \sqrt{\frac{1}{\rho_0 \beta_s}}$$

is the acoustic speed, $\rho_0$ is the density of the medium at rest, and $\beta_s$ is the adiabatic compressibility of the medium. We have assumed that $\tilde{B}_1(r,t) \ll B_0(r)$ in the above equation, where $\tilde{B}_1(r,t) = B_1(r)\text{step}(t)$ is the time-varying magnetic field in our experiments and $\text{step}(t)$ is the step function (it equals 1 when t is larger than zero and equals zero otherwise). This is because the time-varying magnetic field is generated by discharging a capacitor for only about 1 microsecond and the current in the coil is approximately proportional to the discharging time. Therefore the current in the coil should not be large enough to produce a magnetic field that is comparable with the static magnetic field. The estimate from our experiments also supports this assumption, as will be shown in the experimental setup section. $\tilde{J}$ in the source term can further be written as the product of a purely spatial and a purely temporal component i.e., $\tilde{J}(r,t)=J(r)\eta(t)$, where $J(r)$ describes the spatial distribution of the induced eddy current density, and $\eta(t)$ describes the shape of the stimulating pulse. Note that $J(r)$ has the unit of $As/m^2$. Here we consider $J(r)$ to be the induced eddy current since the current generated by excitable membranes within a biological system is in the frequency of several KHz while the induced current in MAT-MI used for image reconstruction is in a much higher frequency range. We consider only the case that the stimulating pulse is very short $\eta(t) \approx \delta(t)$. In experiments, the temporal profile of the induced current includes a strong short positive peak (μs) and a small long negative tail (ms). The net area under the profile is zero. But if we measure only the part of the signal that is within a short time after the positive peak (for example 100 μs), the net area under this portion of profile is positive and we can approximate this profile as a delta function. In the following estimate on the pressure, we have $J(r) \approx \tilde{J}_{ave}(r)\tau$ by using $J(r)=\int_0^{+\infty} \tilde{J}(r,t)dt$, where $\tau$ is the excitation pulse length and $J_{ave}(r)$ is the average current density during the excitation.

After using Green's function, the solution of Eq. 2 can be written as (Morse and Feshbach 1953)

$$\tilde{p}(r, t) = -\frac{1}{4\pi} \oint_V dr' \nabla_{r'} \cdot [J(r') \times B_0(r')] \frac{\delta(t - R/c_s)}{R}, \qquad (3)$$

where $R=|r-r'|$ and the integration is over the sample volume. The physical meaning of this equation is that, in an acoustically homogenous medium, the pressure p, at a spatial point r and time t, is proportional to the integration of $\nabla \cdot (J \times B_0)$ over a spherical surface [a circle in the 2-D case]. The spherical surface is centered at r and has a radius of $tc_s$. Applying integration by parts to Eq. 3, we have $$\tilde{p}(r, t) = \frac{1}{4\pi} \oint_V dr' J(r') \times B_0(r') \cdot \nabla_{r'} \frac{\delta(t - R/c_s)}{R}. \qquad (4)$$

Using $\nabla_{r'} = -\nabla_r$, we have $$\tilde{p}(r, t) = \frac{-1}{4\pi} \oint_V dr' J(r') \times B_0(r') \cdot \nabla_r \frac{\delta(t - R/c_s)}{R}. \qquad (5)$$

Now the differentiation over r can be moved out of the integration and we have $$\tilde{p}(r, t) = -\frac{1}{4\pi} \nabla \cdot \oint_V dr' J(r') \times B_0(r') \frac{\delta(t - R/c_s)}{R}. \qquad (6)$$

This equation is easier to compute in the theoretical analysis and numerical simulations.

B. Inverse Problem of MAT-MI

B.1 Estimation of $\nabla \cdot (J \times B_0)$

The inverse problem can be divided into two steps. In the first step, we will reconstruct $\nabla \cdot (J \times B_0)$ from pressure. In the second step, we will reconstruct the conductivity distribution from $\nabla \cdot (J \times B_0)$. The first step can be accomplished with back-projection algorithm or to solve the spherical Radon transform. The reconstruction step from $\nabla \cdot (J \times B_0)$ to σ is more challenging. The total electrical field in the sample can be divided into two parts $$E = E_{ext} + E_{rsp}, \qquad (10)$$

where the first part $E_{ext}$ represents the solenoid electrical field induced directly by the changing magnetic field, and $E_{rsp}$ represents the electrical field caused by the conductivity heterogeneity of the sample (Malmivuo and Plonsey 1995). It is of electrostatic nature, so it can be expressed as the gradient of a scalar potential $$E_{rsp} = -\nabla \phi. \qquad (11)$$

$E_{ext}$ can be computed easily when the coil configuration is known. However, $E_{rsp}$ can not be measured from experiments. The challenge in the reconstruction step from $\nabla \cdot (J \times B_0)$ to σ lie in how to derive σ without using $E_{rsp}$.

Assume we can measure the acoustic signals across a surface Σ around the to-be-imaged object. Let's consider Eq. 2 for the case of $\tilde{J}(r,t)=J(r)\delta(t)$. After integrating both sides of Eq. 2 over the time range $(-\infty,0^+)$, where $0^+$ is an infinitely small real, we have $$-\frac{1}{c_s^2} \frac{\partial \tilde{p}}{\partial t}\bigg|_{t=0^+} = \nabla \cdot (J \times B_0). \qquad (12)$$

The spatial derivative term disappears in the integration because the pressure is zero before time zero. Eq. 12 means that we can obtain $\nabla \cdot (J \times B_0)$ if we can derive $$-\frac{1}{c_s^2}\frac{\partial \tilde{p}}{\partial t}\bigg|_{t=0^+}.$$

from the pressure measured over the surface Σ. In an acoustically homogeneous medium, this step can be accomplished by time reversing the acoustic waves using Eq. 15 in (Xu and Wang 2004) as $$\tilde{p}'(r, 0^+) \approx \frac{1}{2\pi c_s}\iint_\Sigma dS_d \frac{n\cdot(r_d-r)}{|r-r_d|^2}\tilde{p}''(r_d, |r-r_d|/c_s), \quad (13)$$

where $r_d$ is a point on the detection surface Σ, r is a point in the object space, and the single and double prime represent the first and second derivative over time, respectively. In deriving Eq. 13 we have ignored the first term in the integrand on the right hand side of Eq. 15 in (Xu and Wang 2004), because it is much smaller than the second term in the MHz range. Combining Eq. 12 and Eq. 13, we have $$\nabla\cdot(J\times B_0) \approx \frac{-1}{2\pi c_s^3}\iint_\Sigma dS_d \frac{n\cdot(r_d-r)}{|r-r_d|^2}\tilde{p}''(r_d, |r-r_d|/c_s). \quad (14)$$

This is a back-projection algorithm, in which the pressure at each time point is projected (assigned) to each point on the sphere over which the integration of the object value yields the pressure.

Alternative, the $\nabla\cdot(J\times B_0)$ term can also be estimated by solving Eq. 3 using the inverse Radon transform. Multiplying both sides of equation (3) with $(-4\pi)t$, we can get Eq. (15):

$$g(r, \bar{t}) = \int_V dr'\cdot \nabla\cdot(J(r')\times B_0(r'))\cdot\delta(\bar{t}-|r-r'|) \quad (15)$$

where $\bar{t}=c_s t$. Here $g(r, \bar{t})=(-4\pi)t*\tilde{p}(r,t)$ and can be interpreted as a spherical radon transform of the vibration source $\nabla\cdot(J(r')\times B_0(r'))$. Equation (15) has the same mathematic form as the imaging model of the reflectivity tomography (Pan et al., 2003). The reconstruction of the vibration source thus can be accomplished by inverting the spherical Radon transform via using a reflectivity tomography reconstruction algorithm such as the expectation maximization (EM) algorithm (Pan et al., 2003) as shown in Eq. (16)

$$f^{(n+1)}(x) = \frac{f^{(n)}(x)}{\int_{D_y} h(x,y)dy}\int_{D_y} dy \frac{h(x,y)g(y)}{\int_{D_x} h(x,y)f^{(n)}(x)dx} \quad (16)$$

where n is the number of iteration, f(x) is the source function defined in domain Dx, in the MAT-MI case $f(x)=\nabla\cdot(J(r')\times B_0(r'))$, which is defined in the source volume V as in Eq. (15). In equation (16), h(x,y) is the kernel of the spherical Radom transform, as in (15) it is the item $\delta(\bar{t}-|r-r'|)$. g(y) is the measured data defined in the domain Dy, corresponding to $g(r,\bar{t})$ in Eq. (15), which is the product of the measured ultrasound data with $(-4\pi)t$ in the case of MAT-MI.

B.2 Estimation of Electrical Impedance

Consider a piece-wise homogeneous conductive medium. In this method, we do not need to change the direction of the static magnetic field $B_0$ because only one set of measurement is needed. First, according to Faraday's law, $$\nabla\times\tilde{E} = -\frac{\partial\tilde{B}_1}{\partial t}. \quad (17)$$

Using $\tilde{B}_1(r,t)=B_1(r)\text{step}(t)$, we have $\tilde{E}(r,t)=E(r)\delta(t)$, where E is the spatial component of the electrical field and obeys $$\nabla\times E=-B_1. \quad (18)$$

Combing Eq. 18 with $J=\sigma E$, we have $$\nabla\times(J/\sigma)=-B_1. \quad (19)$$

After expanding the cross product, we have $$(\nabla\times J)/\sigma + \nabla\left(\frac{1}{\sigma}\right)\times J = -B_1. \quad (20)$$

If we assume the sample is piecewise smooth, then we have $|\nabla\sigma|/\sigma\ll|\nabla\times J|/|J|$ except at the boundary points, therefore the second term in Eq. 20 can be ignored and we take an inner product of both sides of Eq. 20 with $B_0$, we have $$\sigma \approx -\frac{(\nabla\times J)\cdot B_0}{B_1\cdot B_0} = -\frac{\nabla\cdot(J\times B_0)}{B_1\cdot B_0} \quad (21)$$

for the points inside a smooth piece, where we replace $(\nabla\times J)\cdot B_0$ with $\nabla\cdot(J\times B_0)$ after using $\nabla\times B_0=0$ for the point in the sample due to the fact that the magnetic field is generated by the sources outside the sample. $\nabla\cdot(J\times B_0)$ can be obtained from pressure according to Eq. 14. Eq. 21 does not hold on the boundary between regions with different conductivity. Therefore we have to distinguish the internal smooth point from the boundary point, where $|\nabla\sigma|/\sigma>|\nabla\times J|/|J|$. The result given by Eq. 21 can be improved iteratively by the following algorithm:

$$\sigma_n = \frac{-(\nabla\times J)\cdot B_0}{[B_1+\nabla(1/\sigma_{n-1})\times J_{n-1}]\cdot B_0}, \quad (22)$$

where $(\nabla\times J)\cdot B_0$, $B_0$, and $B_1$ are measured or derived from measurement in the experiments, $\sigma_{n-1}$ and $\sigma_n$ are the conductivity distribution obtained after the (n−1)-th and n-th iteration, respectively, and $J_{n-1}$ is the computed current distribution corresponding to $\sigma_{n-1}$. To start the iteration, $\sigma_0$ is given by Eq. 21. Then for the given $\sigma_{n-1}$ and boundary conditions, $J_{n-1}$ can be computed by solving the forward linear system of equations using the conjugate gradient method for sparse matrix. After that, the conductivity will be updated according to Eq. 22 in each iteration until a stopping condition is met.

Alternatively, a median filter can be applied to the results of Eq. 21 to smooth out the estimate using Eq. 21.

For a general medium, we need to change the direction of the static magnetic field $B_0$. According to $\omega\epsilon/\sigma\ll 1$ and Ampere's law, we have $$\nabla\cdot J=0. \quad (22)$$

$B_0\cdot(\nabla\times J)$ can be reconstructed from the pressure measured around the objects. Therefore if we make three sets of measurements, where $B_0$ is along three perpendicular directions, we can determine $\nabla\times J$. After combining the boundary condition J·n|_Σ=0 and Eq. 23, J can be determined. Then we take an inner product of both sides of Eq. 20 with J, we have $$\sigma = -\frac{(\nabla \times J) \cdot J}{B_1 \cdot J}. \quad (24)$$

For an inhomogeneous medium, this method is more accurate. But it is obviously more challenging, because there are more intermediate steps, which makes the problem complex. At last, it should be pointed out that the above two methods (Eqs. 21 and 24) are unique to MAT-MI, because both of them require $B_1 = -\nabla \times E \neq 0$. Magnetic induction can satisfy this requirement, but electrical stimulation cannot.

An Experimental Study of MAT-MI

Figure 7:
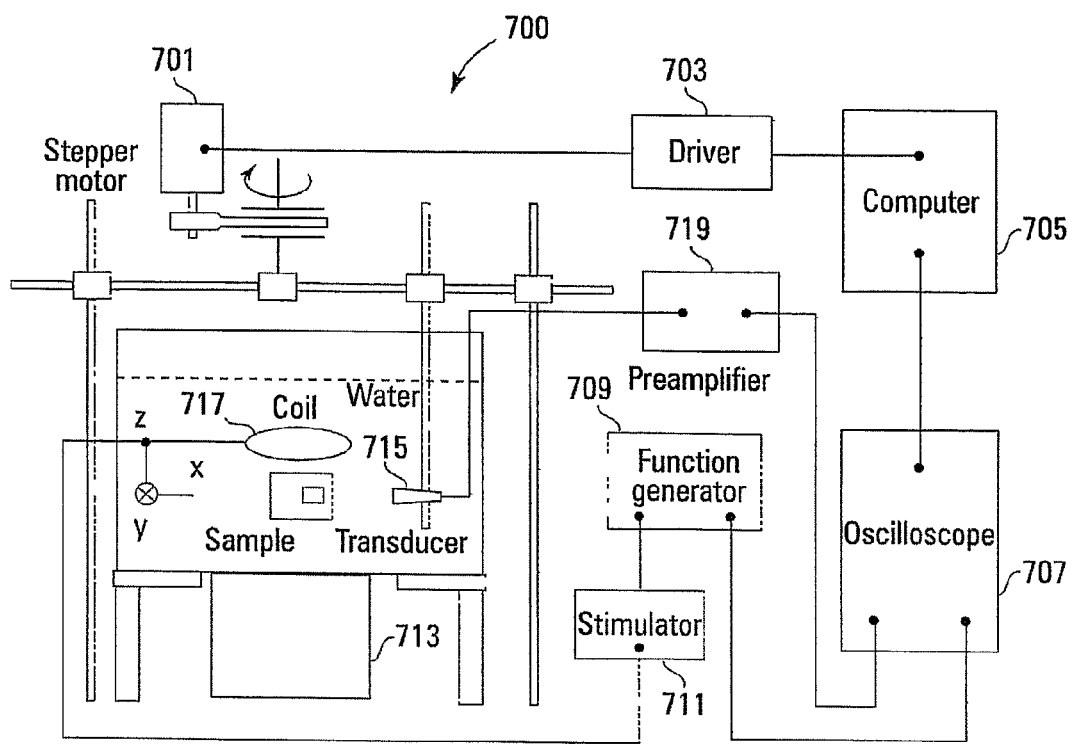
FIG. 7 is an illustration of an apparatus including a stepper motor, a driver. a computer, an oscilloscope, a function generator, a stimulator, a magnet, a transducer, a coil, and a preamplifier in accordance with some embodiments.

FIG. 7 is an illustration of an apparatus 700 including a stepper motor 701, a driver 703, a computer 705, an oscilloscope 707, a function generator 709, a stimulator 711, a magnet 713, a transducer 715, a coil 717, and a preamplifier 719 in accordance with some embodiments. The transducer 715 may be focused or unfocused. In some embodiments, the transducer 715 has a central frequency of 1 MHz and a diameter of 13 mm. In some embodiments, the transducer 715 points horizontally to the sample. For good coupling of acoustic waves, both the transducer and the sample are immersed in water. In some embodiments, the transducer 715 scans around the object in a circular orbit with a radius of 130 mm. The step size of the scanning can be 2.5 degrees.

A magnetic inductor induces electric pulses with a width of 1.2 μs at the rate of 4 Hz. The circular coil of the magnetic inductor has a radius of 40 mm. A single-turn coil with a radius of $r_c=4$ cm is used to estimate the induced electrical field in the space, $E_{ind}$. In the experiments, the electrical field induced by the circular coil of the magnetic inductor is symmetrical and oriented in circular loops around the axis of the inductor coil, while the probe coil is located concentrically with the stimulator coil. Therefore, the probe coil approximately fits into one of the electrical field lines (loops). Consequently, $E_{ind}=V/(2\pi r_c)$, where V is the voltage measured over the probe coil. The induced electrical field right around the coil of the inductor is measured to be about 250 Vm$^{-1}$ while the induced electrical field at the position of the samples in the experiments (about 5 cm away from the coil of the inductor) is measured to be around 25 Vm$^{-1}$. According to the measured electrical field, the estimate the final magnitude of the time-varying magnetic field at the sample's position is $B_1=2\tau E_{ind}/r_c=0.00125$ T after considering $$\frac{d(B_1 \cdot \pi r_c^2)}{dt} = -E_{ind} \cdot 2\pi r_c$$

and $E_{ind}$ is almost constant during the excitation period.

A permanent magnet (50 mm by 50 mm by 25 mm) is placed put around 2 cm under the sample. The permanent magnet can create a magnetic field along the z-axis with a flux density of about 0.1 T at 2 cm from its surface. A function generator is used to trigger the magnetic inductor, control its pulse length, and synchronize the oscilloscope sampling. The signal from the transducer is first amplified, then recorded and averaged 100 times by a software oscilloscope (National Instruments, Austin). A personal computer is used to control the step motor for scanning the detector and transferring the data. A multifunctional card in the computer acted as the function generator, oscilloscope, and part of the driver for the stepper motor.

Figure 8A:
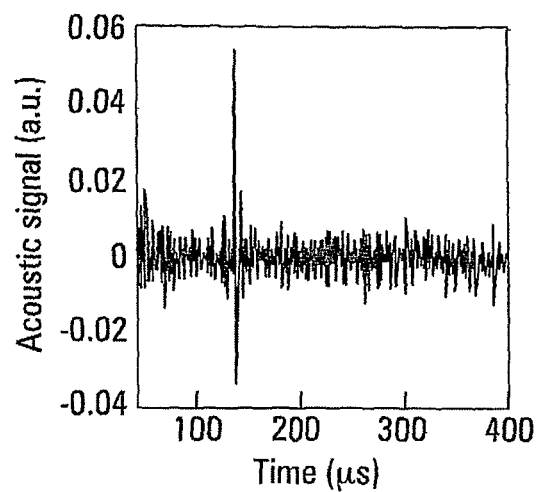
FIGS. 8(a) and 8(b) illustrate a peak observed in the signals after high-pass filtering in accordance with some embodiments.
Figure 8B:
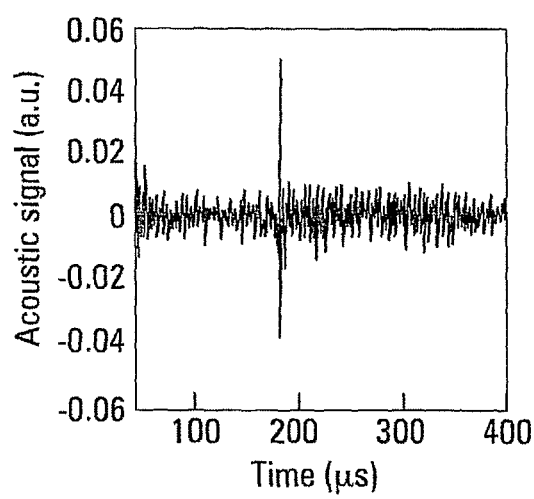

In this experiment, we used a copper stripe with a section of 1 mm by 4 mm as the sample for observing the MAT-MI signals. The long dimension of the strip is perpendicular to the scanning plane. FIGS. 8(a) and 8(b) illustrate a peak observed in the signals after high-pass filtering in accordance with some embodiments. When we moved the copper back and forth, the peak also moved accordingly, as shown by comparing FIG. 8(a) and FIG. 8(b). We also moved the detector around the copper. In most positions, we can detect the signal from the copper although the amplitude of the signal varies. Basically, the amplitude of the signal increased when the detector moved closer to the object.

Then we imaged a close metal loop, which is made from a 0.5 mm diameter metal wire. We did not observed any signal due to the scattering by the wire. FIG. 9 is an illustration of a signal that results from wire scattering. There are two major peaks with a time delay of about 30 μs, which matches with the distance between the front and rear boundary of the loop when looking from the position of the transducer. This shows that the two major peaks correspond to the two boundaries. When we moved the detector around the object, the signal looks similar except that the time delay between the two peaks is different.

FIGS. 10(a) and 10(b) illustrate an image of a wire loop and the wire loop, respectively. MAT-MI and the photo of a metal wire loop. The center of the image is the origin of the circular scanning orbit of the transducer. The reconstructed image represents the boundary of $\nabla \cdot (J \times B_0)$ induced by the magnetic induction in the sample. Therefore we compare only the size and shape of the loop in the MAT-MI image and the corresponding photo and we find they are in good agreement.

Imaging electrical impedance with noninvasive measurements is important to various biomedical applications. A number of efforts have been made to probe the physiological or pathological status of biological systems from the information on the electrical impedance of tissues. Such impedance information on the biological tissues may also be useful to other biomedical research such as electric source imaging, in which electromagnetic measurements are made over the body surface or out of the body while the tissue impedance information is necessary to solve the forward problem (He 2004; He and Lian, 2005).

Under the acoustic homogeneity assumption, we have derived explicit theoretical formulas governing MAT-MI. This theoretical development is important because it offers a well-posed problem to solve the electrical-impedance imaging problem. In many other impedance imaging approaches such as EIT, the inverse problem is ill-posed which limits the spatial resolution of the methods.

Embodiments for Cancer Detection and Treatment

In one embodiment, a subject is placed in a static magnetic field and a single or multiple magnetic pulse are applied to induce the acoustic signals. The said acoustic signals are detected by a single or multiple acoustic detectors sequentially spaced at a multiplicity of locations in the space, or by an array of acoustic detectors over the space simultaneously. The said acoustic signals are then used to reconstruct the images of electrical impedance within the body. The electrical impedance images are displayed on a displaying device to aid diagnosis and treatment of tumors such as cancer.

In another embodiment, a subject is placed in a MRI scanner and a single or multiple magnetic pulses are applied to induce the acoustic signals. The acoustic signals are detected by a single or multiple acoustic detectors sequentially spaced at a multiplicity of location in the space, or by an array of acoustic detectors over the space. The subject will also undergo a regular MRI scan. The acoustic signals are used to reconstruct the images of electrical impedance within the body, and coregistered with the structure MRI of the subject. The electrical impedance images are displayed together with the subject's MRI images to aid diagnosis and treatment of tumors such as cancer.

In another embodiment, a subject is placed in a magnetic field and a single or multiple magnetic pulses are applied to induce the acoustic signals. The acoustic signals are detected by a single or multiple acoustic detectors sequentially spaced at a multiplicity of locations in the space, or by an array of acoustic detectors over the space simultaneously. The subject will also undergo a regular computer tomography (CT) scan. The acoustic signals are used to reconstruct the images of electrical impedance with the body, and coregistered with the CT images of the subject. Such electrical impedance images are displayed together with the subject's CT images to aid diagnosis and treatment of tumors such as cancer.

In another embodiment, a subject is placed in a magnetic field and a single or multiple magnetic pulses are applied to induce the acoustic signals. The acoustic signals are detected by a single or multiple acoustic detectors sequentially spaced at a multiplicity of locations in the space, or by an array of acoustic detectors of the space simultaneously. The said acoustic signals are used to reconstruct the images of electrical currents within the body, and coregistered with other images of the subject such as MRI or CT images. The electrical current images are displayed together with the subject's structure images to aid diagnosis and treatment of tumors such as cancer.

In another embodiment, a subject is placed in a magnetic field and a single or multiple magnetic pulses are applied to induce the acoustic signals. The acoustic signals are detected by a single or multiple acoustic detectors sequentially at a multiplicity of locations in the space, or by an array or of acoustic detectors over the space simultaneously. The acoustic signals are used to reconstruct the images of electrical currents and electrical impedance within the body, and coregistered with other images of the subject such as MRI or CT images. The images of electrical currents and electrical impedance are displayed together with the subject's anatomical images to aid diagnosis and treatment of tumors such as cancer.

In another embodiment, a subject is placed in a magnetic field and a single or multiple magnetic pulses are applied to induce the acoustic signals. The acoustic signals are detected by a single or multiple acoustic detectors sequentially at a multiplicity of locations in the space, or by an array of acoustic detectors over the space simultaneously. The acoustic signals are used to reconstruct the images of mechanical properties of the tissues, such as stiffness, mechanical impedance, within the body, and coregistered with other images of the subject such as MRI or CT images. Such images of mechanical properties are displayed together with the subject's anatomical images to aid diagnosis and treatment of tumors such as cancer.

In another embodiment, a subject is placed in a magnetic field and a single or multiple magnetic pulses are applied to induce the acoustic signals. The acoustic signals are detected by a single or multiple acoustic detectors sequentially at multiplicity of locations in the spaces, or by an array of acoustic detectors over the space simultaneously. The acoustic signals are then used to reconstruct the images of mechanical and electrical properties of the tissues, within the body, and coregistered with other images of the subject such as MRI or CT images. The images of electrical and mechanical properties are displayed together with the subject's anatomical images to aid diagnosis and treatment of tumors such as cancer.

In another embodiment, a subject is placed in a static magnetic field, a single or multiple acoustic energies are delivered to the subject and magnetic field produced due to the administration of the acoustic signals are recorded. The magnetic signals are used to reconstruct the images of electrical impedance or electrical currents, or other electrical properties of the tissues, or mechanical properties of the tissues. The images are displayed on a displaying device to aid diagnosis and treatment of tumors such as cancer.

In one embodiment, a subject is undergoing the above procedures to diagnose breast cancer, lung cancer, oral cancer, colon cancer, liver cancer, brain cancer, or other cancers.

Embodiments for Aiding Diagnosis and Surgical Planning

In one embodiment, a subject is placed in a static magnetic field and a single or multiple magnetic pulses are applied to induce the acoustic signals. The acoustic signals are detected by a single or multiple acoustic detectors sequentially at a multiplicity of locations in the space, or by an array of acoustic detectors over the space simultaneously. Furthermore, the electrical activity of the said subject is recorded by an array of electrode sensors over part of the body or by an array of magnetic sensors out of the body. The acoustic signals are used to reconstructed the images of electrical impedance within the body. The electrical or magnetic signals produced by the subject are used in conjunction with the electrical impedance information estimated from the acoustic signals, to reconstruct distribution of electrical sources within the body. Such electrical source images are displayed on a displaying device to aid diagnosis or surgical planning.

In one embodiment, a subject is placed in a MRI scanner and a single or multiple magnetic pulses are applied to induce the acoustic signals. The acoustic signals are detected by a single or multiple acoustic detectors sequentially at a multiplicity of locations in the space, or by an array of acoustic detectors over the space simultaneously. Furthermore, the electrical activity of the subject is recorded by an array of electrode sensors over part of the body or by an array of magnetic sensors out of the body. The acoustic signals are used to reconstruct the images of electrical impedance within the body. The electrical or magnetic signals produced by the subject are used in conjunction with the electrical impedance information estimated from the acoustic signals, to reconstruct distribution of electrical sources in the body. Such electrical source images are coregistered with MRI images and displayed on a displaying device to aid diagnosis or surgical planning.

In one embodiment, a subject is placed in a static magnetic field and a single or multiple magnetic pulses are applied to induce the acoustic signals. The acoustic signals are detected by a single or multiple acoustic detectors sequentially at a multiplicity of locations in the space, or by an array of acoustic detectors over the space simultaneously. Furthermore, the electrical activity of the subject is recorded by an array of electrode sensors over part of the body or magnetic sensor out of the body. The acoustic signals are then used to reconstruct the images of electrical properties such as electrical impedance or currents or others within the body. The electrical or magnetic signals produced by the subject are used in conjunction with the electrical properties information estimated from the acoustic signals to reconstruct distribution of electrical sources in the body. Such electrical source images are displayed on a displaying device to aid diagnosis or surgical planning or catheter ablation procedures.

In one embodiment, a subject is placed in a static magnetic field and a single or multiple magnetic pulses are applied to induce the acoustic signals. The acoustic signals are detected by a single or multiple acoustic detectors sequentially at a multiplicity of locations in the space, or by an array of acoustic detectors over the space simultaneously. Furthermore, the electrical activity of the subject is recorded by an array of electrode sensors over part of the body or by an array of magnetic sensors out of the body. The acoustic signals are then used to reconstruct the images of electrical properties or mechanical properties within the body. The electrical or magnetic signals produced by the said subject are used in conjunction with the electrical or mechanical properties information estimated from the acoustic signals, to reconstruct distribution of electrical sources in the body. And such electrical source images are coregistered with other imaging results such as MRI or CT and displayed on a displaying device to aid diagnosis or surgical planning.

In another embodiment, a subject is placed in a static magnetic field, a single or multiple acoustic energies are delivered to the subject and magnetic field produced due to the administration of the acoustic signals are recorded. The magnetic signals are used to reconstruct the images of electrical properties of the tissues, or mechanical properties of the tissues. The images are then displayed on a displaying device to aid diagnosis or surgical treatment.

In one embodiment, a subject is undergoing the above procedures to aid presurgical planning, surgical planning in epilepsy patients or brain tumor patients.

In one embodiment, a subject is undergoing the above procedures to aid catheter ablation in patients with cardiac arrhythmias.

Embodiments for Imaging Eddy Currents

In one embodiment, a subject is placed in a static magnetic field and a single or multiple magnetic pulses are applied to induce the acoustic signals. The acoustic signals are detected by a single or multiple acoustic detectors sequentially at multiplicity of locations in the space, or by an array of acoustic detectors over the space simultaneously. The acoustic signals are used to reconstruct the distribution of eddy currents within the body. Such eddy current images are displayed on a displaying device to aid treatment of epilepsy, mental diseases, and other neurological disorders.

In another embodiment, a subject is placed in a magnetic field and a single or multiple magnetic pulses are applied to induce the acoustic signals. The acoustic signals are detected by a single or multiple acoustic detectors sequentially at a multiplicity of locations in the space, or by an array of acoustic detectors over the space simultaneously. The acoustic signals are then used to reconstruct the images of eddy currents within the body, and coregistered with other medical imaging results such as MRI or CT images of the subject. Such eddy current images are used to determine the parameters of magnetic stimulators, internal or eternal to the body, for the purpose of treating diseases such as neurological, mental, and cardiovascular diseases.

In one embodiment, a subject is undergoing the above procedures to aid treatment for brain diseases such as epilepsy, Parkinson's disease, or depression.

In one embodiment, a subject undergoing the above procedures to aid treating cardiac arrhythmias.

Other Embodiments

In one embodiment, an object is placed in a static magnetic field and an array of pulsed magnetic field generators are placed surrounding the object to generate multiple magnetic pulsed fields in series or in parallel to induce the acoustic signals. The acoustic signals are detected by a single or multiple acoustic detectors sequentially at a multiplicity of locations in the space, or by an array of acoustic detectors over the space simultaneously. The acoustic signals are used to reconstruct the information regarding electrical impedance, or other electrical properties, or mechanical properties within the body. Distributions of such electrical impedance, or electrical properties or mechanical properties of the tissue are displayed on a displaying device to obtain tissue properties.

In another embodiment, an object is placed in a static magnetic field and an array of alternating magnetic field generators are placed surrounding the object to generate a multiple magnetic pulsed field in series or in parallel with the same or different frequencies for theses magnetic field generators. The acoustic signals are generated within the tissue according to the fundamental physics and detected by a single or multiple acoustic detectors sequentially at a multiplicity of locations in the space, or by an array of acoustic detectors over the space simultaneously. The acoustic signals are used to reconstruct the information regarding electrical impedance, or other electrical properties, or mechanical properties within the body. Distributions of such electrical impedance or electrical property or mechanical property of the tissue are displayed on a displaying device to obtain tissue properties.

In another embodiment, an object is placed in a static magnetic field and an array of pulsed or alternating magnetic field generators are placed surrounding the object to generate multiple magnetic pulsed field. The array of the pulsed or alternating magnetic field generators can further rotate surrounding the object in series or in parallel with the same or different frequencies for these alternating magnetic field generators. The acoustic signals are generated within the tissue according to the fundamental physics and detected by a single or multiple acoustic detectors sequentially a multiplicity of locations in the space, or by an array of acoustic detectors over the space simultaneously. Such an array of acoustic signal detectors can further rotate surrounding the object. The acoustic signals are processed to extract information regarding electrical impedance, or other electrical properties, or mechanical properties within the body. The distribution of such electrical impedance or electrical properties or mechanical properties of the tissue are displayed on a displaying device to obtain tissue properties.

In one embodiment, the object is a biological system. In another embodiment, the object is a human subject. The said images of electrical impedance, or other electrical properties, or mechanical properties are used to detect or diagnose breast cancer or other cancers, to aid surgical planning of neurological diseases, to aid catheter ablation or cardiac arrhythmias, or to aid the diagnosis and treatment of disorders of a body system.

MAT-MI has several advantages over other imaging techniques. First, MAT-MI will not be affected by the low-conductivity layer of tissue at or near the surface of human body, such as the skull of the head and the fat layer of the breast. This is because the magnetic fields, unlike electrical currents, can go easily into the low-conductivity layer. Second, the electrical field induced by a pulsed magnetic filed in MAT-MI is a solenoid filed, while irrotational fields are used in most other tomography related with the electrical properties, such as EIT or MAT/HEI or MREIT. There are explicit formulas to reconstruct conductivity from acoustic signals in MAT-MI due to this unique feature of solenoid field, as will be shown in the reconstruction methods. Finally, this technique is compatible with an MRI setup but less demanding in terms of field homogeneity and stability.

A Simulation Study of MAT-MI

To evaluate the performance of MAT-MI, we conducted computer simulation studies using a two-layer concentric spherical model, approximating biological tissue (e.g. tumor surrounded by healthy tissue). This simplified geometry model provides an analytical forward solution to simulate the magnetically induced eddy current, but all other procedures are simulated as close as possible to a practical setup.

Simulation Model

Figure 11:
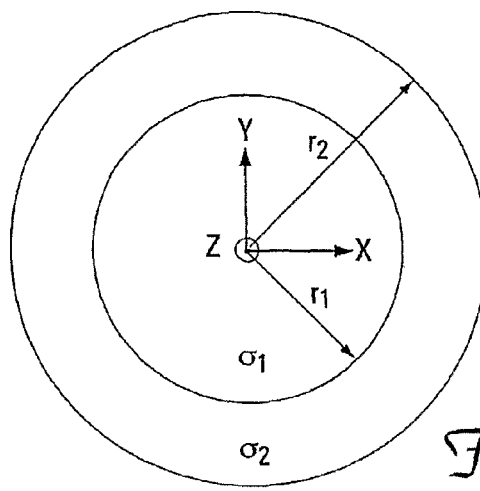
FIG. 11 illustrates a coordinate system.
Figure 12A:
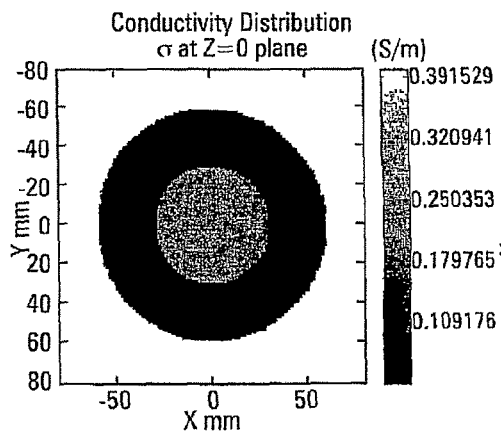
FIGS. 12(a), 12(b), 12(c), and 12(d) illustrate conductivity distributions.
Figure 12B:
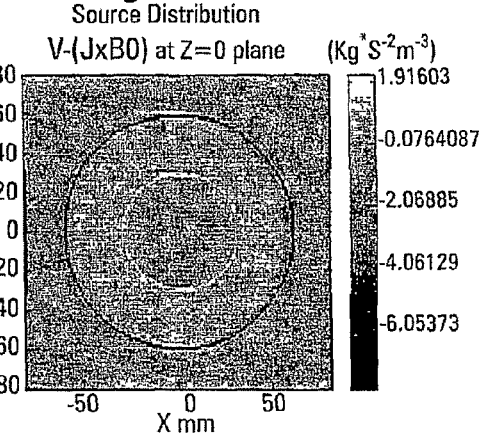
Figure 12C:
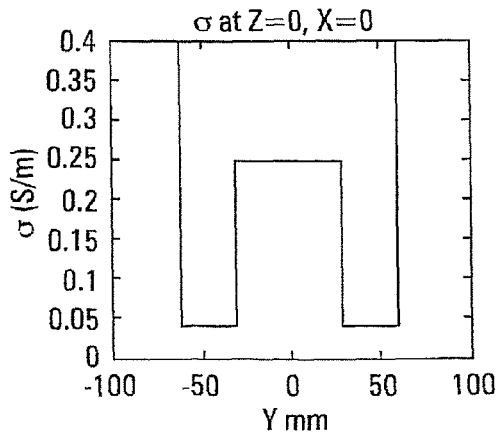
Figure 12D:
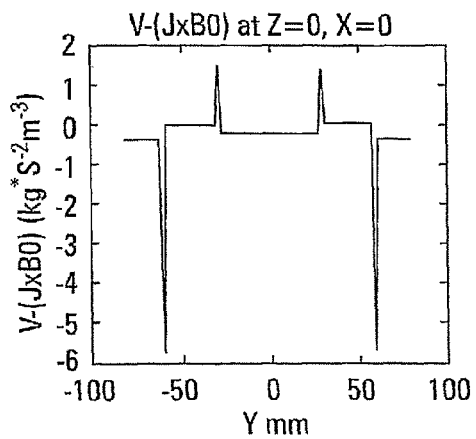
Figure 13A:
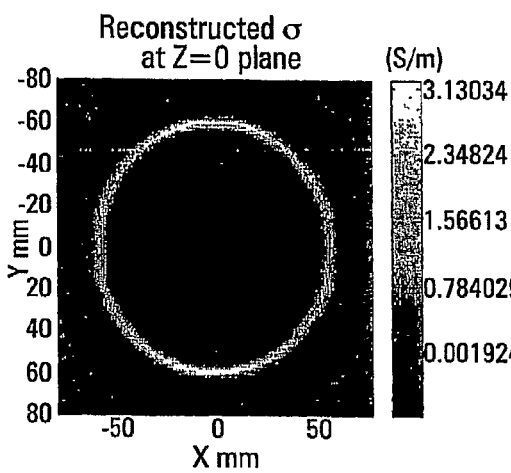
FIGS. 13(a), 13(b), 13(c), and 13(d) illustrate conductivity distributions.
Figure 13B:
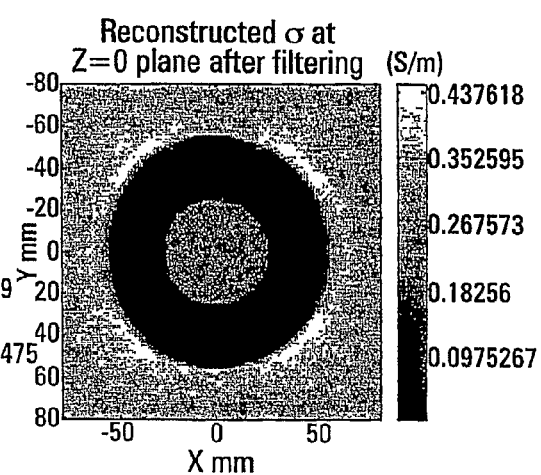
Figure 13C:
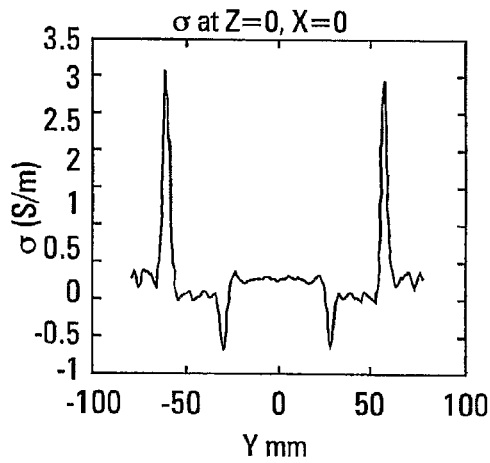
Figure 13D:
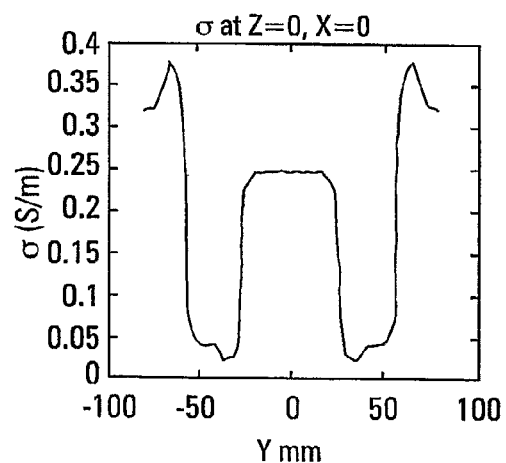

The model geometry is shown in FIG. 11, where $r_1$ and $r_2$ are radii of the inner and outer layers of the spherical conductive object, respectively. $\sigma_1$ and $\sigma_2$ are the corresponding conductivity values of the two layers. $\sigma_3$ is the background conductivity. The coordinate origin is at the spherical center. We assume there is a homogeneous static magnetic field in the whole space domain oriented to the positive Z direction with magnetic flux density of $B_0$. An excitation coil is placed around the sample spheres with its axis in the Z direction and going through the XY plane at point $(0, \alpha)$. For the stimulating magnetic flux density $\tilde{B}_1(r,t)$ produced by the coil, we assume that it is homogeneous, points in the Z direction, and covers a space domain containing the entire conductive object. In addition, we assume that the concentric spheres and the surrounding media are acoustically homogeneous, indicating that the acoustic speed $c_s$ is a constant value and there is no acoustic scattering and attenuation. Under these assumptions, according to the definition of magnetic vector potential and the Coulomb gauge condition, the magnetic vector potential $\tilde{A}$ can be expressed as in equation (25).

$$\tilde{A} = \frac{1}{2}\tilde{B}_1[x\hat{y} - (y-\alpha)\hat{x}] \tag{25}$$

Using the magnetic vector potential $\tilde{A}$, the total electrical field can be expressed as in equation (26).

$$\tilde{E} = -\frac{\partial \tilde{A}}{\partial t} - \nabla \phi \tag{26}$$

The first term on the right hand side of equation (26) represents the electrical field induced directly by the magnetic excitation. The second term on the right hand side of equation (26) represents the electrical field caused by volume conduction in a conductive medium and has an electrostatic nature. The current density can thus be expressed as in equation (27).

$$\tilde{J} = \sigma\tilde{E} = \sigma\left(-\frac{\partial \tilde{A}}{\partial t}\right) + \sigma(-\nabla \phi) \tag{27}$$

Furthermore, in the conductive volume of the sample, we also have equation (28) because there is no external current source and the magnitude of the spontaneous currents generated by biological tissue is much smaller than the induced eddy current.

$$\nabla \cdot \tilde{J} = 0 \tag{28}$$

Combining equations (26)-(28) we can derive the Laplace equation for the electric potential in those areas with homogeneous conductivity, as in (29)

$$\nabla^2 \phi = 0 \tag{29}$$

At conductivity boundaries, we have both the Dirichlet and Neumann boundary conditions:

$$\phi_1 = \phi_2$$
$$J_1 \cdot n = J_2 \cdot n \tag{30}$$

where n is the unit normal vector of the boundary surface. In the concentric spherical model, the solution of the Laplace equation in a spherical coordinate system can be represented in a Legendre series as in equation (31) where $Y_{lm}$ is the Legendre function, and $A_{lm}$, $B_{lm}$, $C_{lm}$ and $D_{lm}$ are coefficients.

$$\phi(r) = \sum_{l=0}^{\infty}\sum_{m=-l}^{l} Y_{lm}(\theta, \eta) \cdot \begin{cases} A_{lm}r^l & \text{if } r < r_1 \\ B_{lm}r^l + C_{lm}r^{-(l+1)} & \text{if } r_1 < r < r_2 \\ D_{lm}r^{-(l+1)} & \text{if } r > r_2 \end{cases} \tag{31}$$

From equations (30)-(31), it can be obtained that only those items with $l=1$ are nonzero in equation (31). Expanding both the Dirichlet and Neumann boundary conditions as in (30) on the two conductivity boundaries in the model, we can get four equations and solve those four coefficients. Note that the conductivity values of the object is reflected in the Neumann conditions and thus influence the calculation of the coefficients on the right hand side of equation (31). After obtaining these coefficients, we can calculate the current density distribution $\tilde{J}$ using equation (27). For the forward solution, the pressure $\tilde{p}$ over all the transducer positions can be simulated. In this simulation model, the detection surface is also a spherical surface surrounding the two-layer spherical sample and centers at the origin. Transducers are uniformly located on this detection surface.

In the inverse simulation, the acoustic source $\nabla \cdot (J \times B_0)$ is first estimated using equation (14). The integration is based on the simulated pressure measurement. Following this, the electrical conductivity is estimated using equation (21).

Simulation Protocol

In the present simulation study, the amplitude of the static magnetic field flux density $B_0$ and the pulsed magnetic field flux density $B_1$ are both set to be 1 Tesla. This is an achievable field level by current commercial MRI system and magnetic stimulator. The acoustic speed is set to be 1.5 mm/μs, which is around the sound speed in water and normal soft tissue. The displacement $\alpha$ is set to 1 mm. Unless there is an explicit description, the radius of the outer sphere $r_2$ is set to 60 mm and the radius of the detection surface is set to 140 mm. The forward and inverse calculation was implemented on a 160×160×160 mm³ cube, with a calculation grid of 1×1×1 mm³. The temporal calculation grid was set to be 0.67 μs, which corresponds to a transducer sampling frequency of 1.5 MHz.

To evaluate the reconstructed conductivity image in this simulation study, Correlation Coefficient (CC), Relative Error (RE), and Average Conductivity Error (ACE) are used. The CC is defined as follows $$CC = \frac{\sum_{n=1}^{N}(\sigma_n - \overline{\sigma}) \cdot (\sigma_{r,n} - \overline{\sigma}_r)}{\sqrt{\sum_{n=1}^{N}(\sigma_n - \overline{\sigma})^2 \cdot \sum_{n=1}^{N}(\sigma_{r,n} - \overline{\sigma}_r)^2}} \tag{32}$$

where $\sigma_n$, $\sigma_{r,n}$ are the target and reconstructed conductivity value for the nth element, and $\overline{\sigma}$, $\overline{\sigma}_r$ are the mean conductivity value for the target and reconstructed image, respectively. N is the number of elements in the image. CC is used to assess the similarity in spatial distribution between the reconstructed and target conductivity images. RE is defined as $$RE = \sqrt{\frac{\sum_{n=1}^{N}(\sigma_n - \sigma_{r,n})^2}{\sum_{n=1}^{N}(\sigma_n)^2}} \quad (33)$$

and is used to estimate the reconstruction error. ACE is defined as $$ACE = \frac{\left|\sigma - \frac{1}{M}\sum_{n=1}^{M}\sigma_{r,n}\right|}{\sigma}. \quad (34)$$

where $\sigma$ is the target conductivity value in the region of interest, $\sigma_{r,n}$ is the reconstructed conductivity value for the nth element and M is the number of elements in the region of interest. ACE can be used to evaluate reconstruction errors in different regions within the piecewise homogeneous conductor model.

Simulation Results

A MAT-MI simulation example using the two layer spherical model is shown in FIGS. 12 and 13. FIG. 12 shows the real conductivity distribution and calculated vibration source $\nabla \cdot (J \times B_0)$ in the Z=0 plane. In this example, the radius of the inner sphere $r_1$ was set to 30 mm and the conductivity values $\sigma_1$, $\sigma_2$ and $\sigma_3$ were set to 0.25, 0.04 and 0.4 S/m respectively. This conductivity configuration is analogous to a piece of muscle embedded in a fat layer which has a lower conductivity value. From FIG. 12, we can see that the vibration source $\nabla \cdot (J \times B_0)$ has large peaks at the boundaries, with each peak extending approximately 3 mm in the spatial dimension. This peak size is related to the numerical calculation grid, while in the continuous case, it would reduce to a pulsed function. In experiments, this is also related to the pulse width of the magnetic excitation pulse sent by the coil. The estimated pressure in this simulation (not shown in figure) was on the order of 0.01 Pascal and is in the detectable range of current commercial transducers. FIG. 13 shows the corresponding reconstructed image of the conductivity distribution, with 4,902 sampling positions. FIGS. 13(a) and (c) are from the direct reconstruction using equations (14) and (21), where the boundary peaks are quite obvious. In addition, there is some projection noise in the background area, which is mainly introduced by the discrete surface integration of the back-projection algorithm given in equation (14). FIGS. 13(b) and (d) resulted from using a median filter with 17 mm widow width on FIGS. 13(a) and (c) to remove the boundary peaks. The CC and RE of the reconstructed image in FIG. 13(a) with the target image in FIG. 12(a) are 0.17 and 1.86, respectively. As a comparison, the corresponding CC and RE of FIG. 13(b) with the target image in FIG. 12(a) are 0.81 and 0.31, respectively. This result indicates that using the median filter can effectively suppress the boundary peaks. However, it is observed in FIG. 13(b) that some boundary shifts are introduced by the use of the median filter.

Figure 14A:
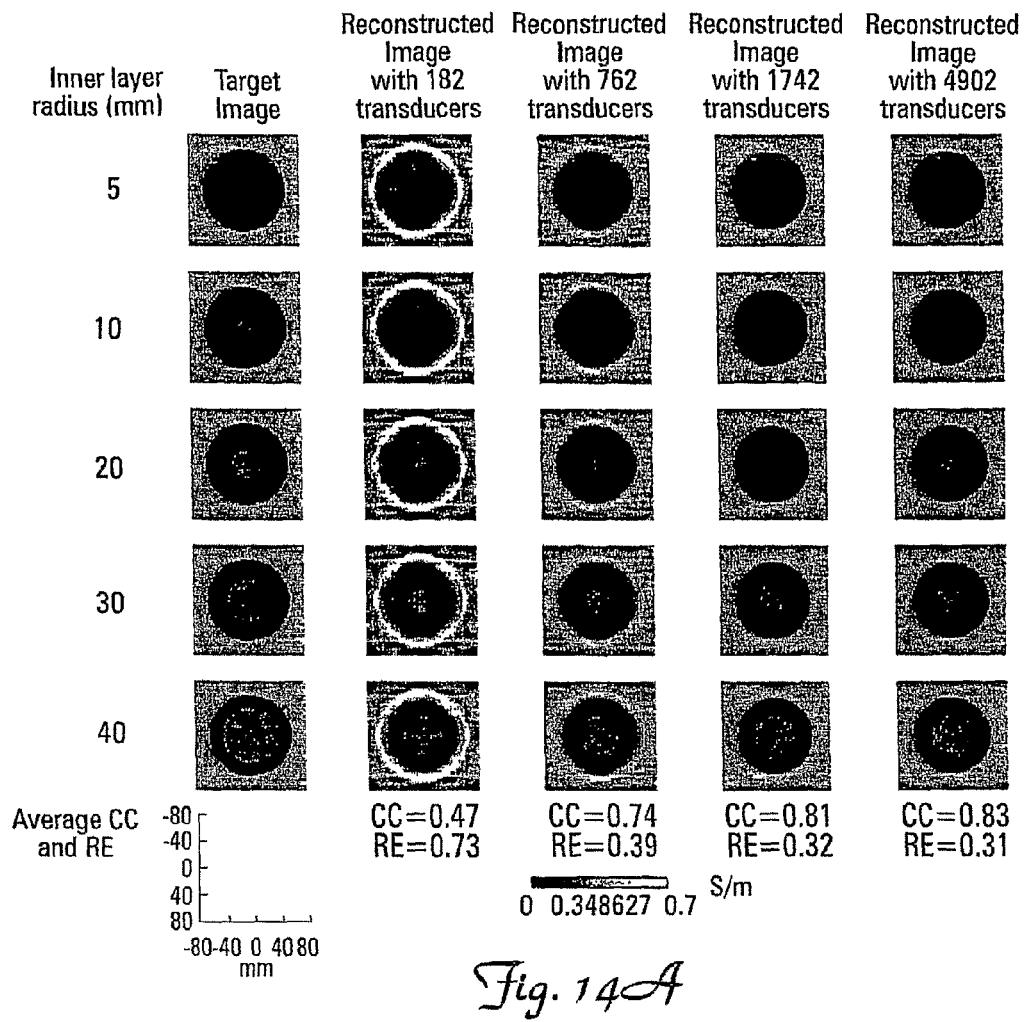
FIGS. 14(a), 14(b), and 14(c) illustrate reconstructed images, correlation coefficients, and relative error, respectively.
Figures 14B, 14C:
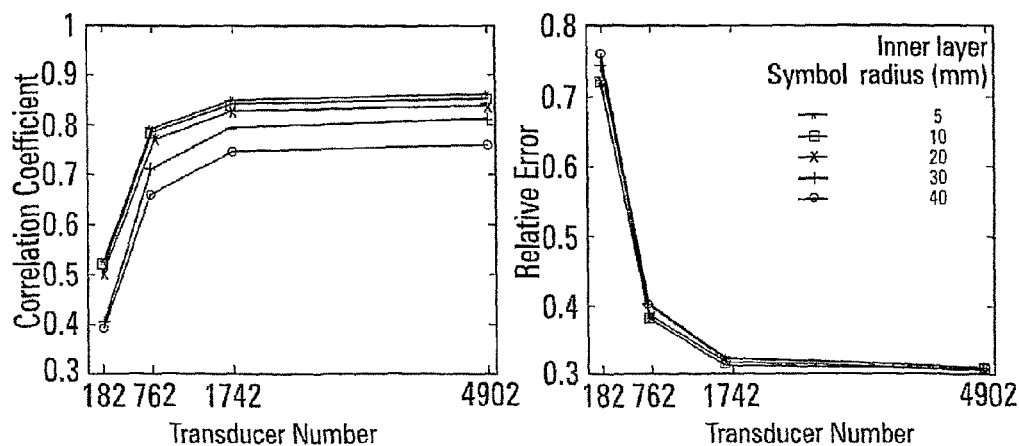
Figure 15:
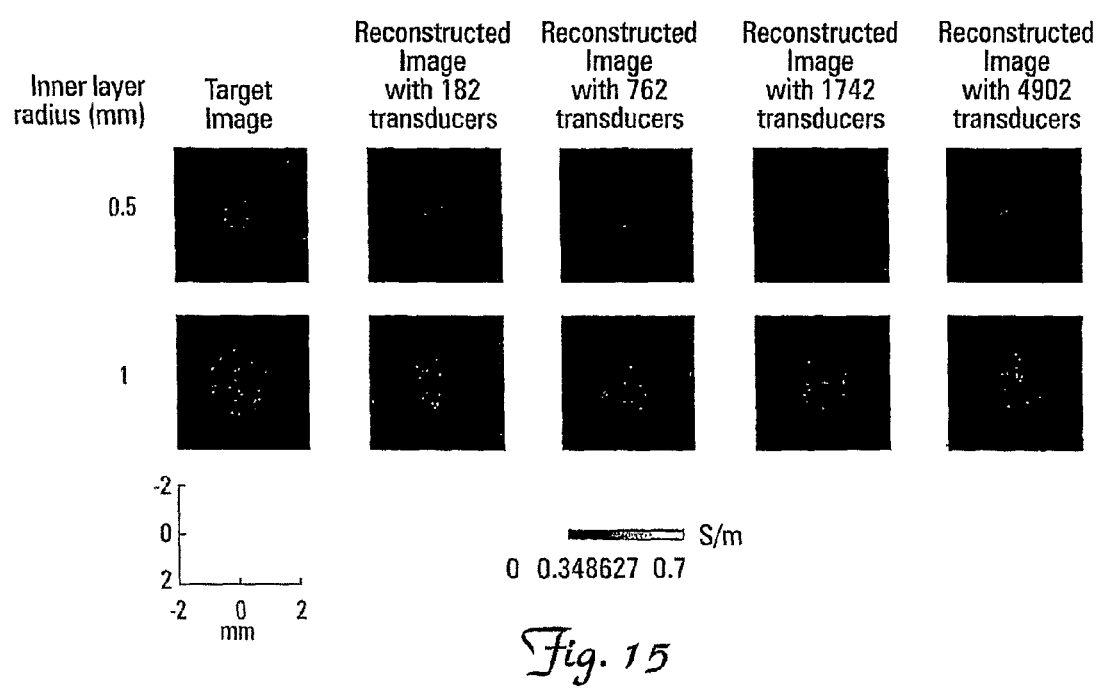
FIG. 15 illustrates target and reconstructed images.

As most back-projection algorithms used in CT, MRI etc, positions used for back-projection in MAT-MI can enhance image quality. Here we use transducer number to represent the amount of sampling positions. The effect of using different numbers of transducers is shown in FIG. 14, where reconstructed images in the Z=0 plane using different numbers of transducers (182, 762, 1742, 4902) are compared with the target conductivity distribution in terms of CC and RE. In this simulation, the radius of the inner sphere $r_1$ was set to be 5, 10, 20 30 and 40 mm and the conductivity values $\sigma_1$, $\sigma_2$ and $\sigma_3$ were set to 0.25, 0.04 and 0.4 S/m respectively. As shown in FIG. 14, when the number of transducers is increased to 4902, the average CC value goes up to 0.83 and the RE value goes down to 0.31. The large RE (even when using a large number of transducers) is mainly caused by the back-projection noise and the boundary shift introduced by the use of the median filter. In addition, it is observed that the median filter and the rough grid size cause a loss of detailed structure in the reconstructed image, as shown in FIG. 14 when the inner layer radius is 5 mm or 10 mm. Thus, to test the performance of MAT-MI in imaging small objects, we used a fine grid of $0.025 \times 0.025 \times 0.025$ mm$^3$ in a $4 \times 4 \times 4$ mm$^3$ cube. The radius $r_1$ was set to be 0.5 and 1 mm respectively in two cases and $r_2$ was set to 1.5 mm. $\sigma_1$ was 0.25 S/m, $\sigma_2$ and $\sigma_3$ were both 0.04 S/m. FIG. 15 displays the results which can be regarded as an enlarged high resolution image for the central part of the images in FIG. 14. The boundary peaks in FIG. 15 extend only 0.2 mm, thus a median filter with a 0.425 mm window width was used in image reconstruction. From the reconstructed image, we can see the small spherical object with radius of 0.5 mm and 1 mm respectively. Reconstructed images using different numbers of transducers are also compared.

Figure 16A:
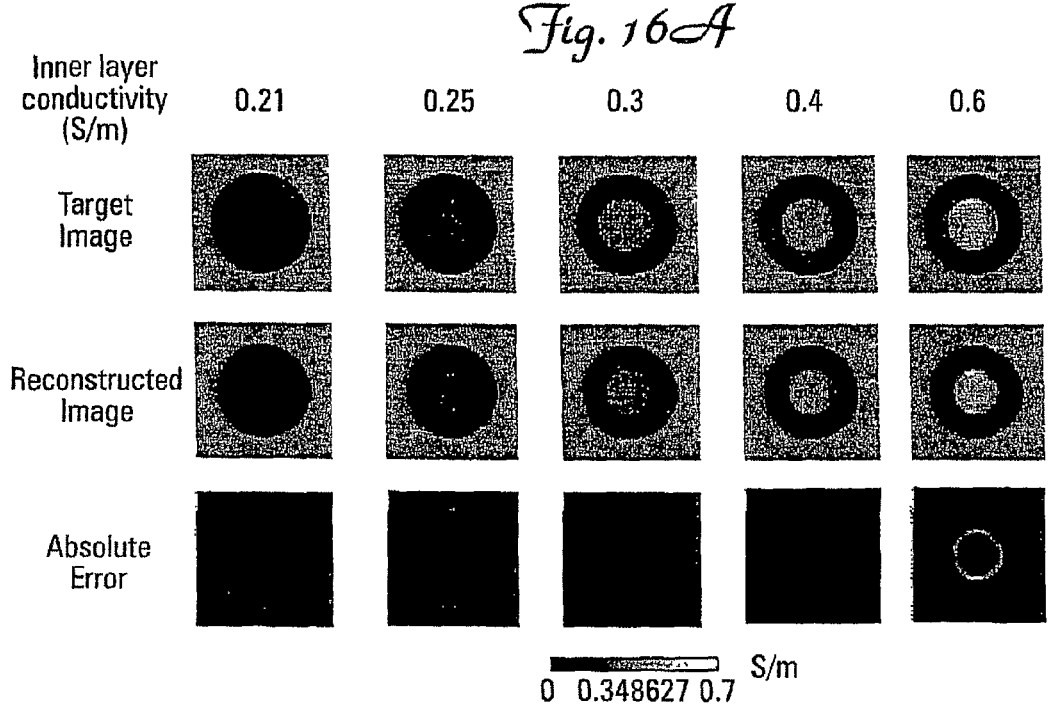
FIGS. 16(a), 16(b), and 16(c) illustrate conductivity and error images, correlation coefficients, and relative error, respectively.
Figure 16B:
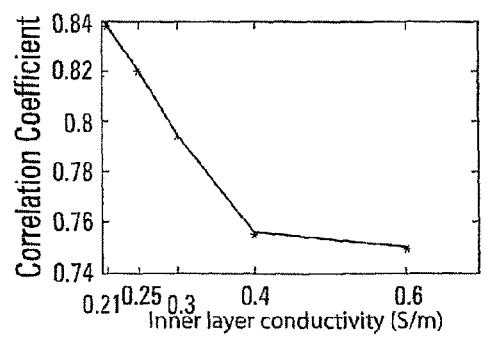
Figure 16C:
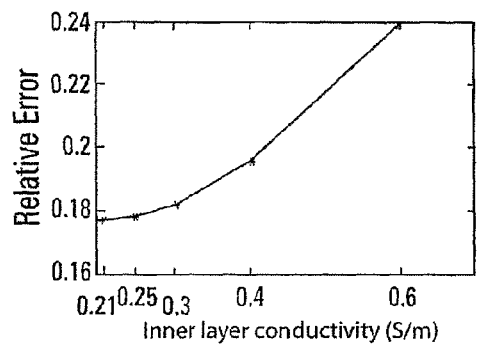

One of the advantageous features of bioimpedance imaging is the good image contrast it can provide. In order to find out how accurately the MAT-MI imaging algorithm can reconstruct the conductivity value of the sample, spherical models with different conductivity contrast were studied. In the spherical model, we set the conductivity value of the inner layer $\sigma_1$ to 0.21, 0.25, 0.3, 0.4 and 0.6 S/m, while the conductivities of the outer layer and surrounding media $\sigma_2$ and $\sigma_3$ were set to 0.2 and 0.4 S/m respectively. The radius of the inner sphere $r_1$ was set to be 30 mm. FIG. 16(a) shows the result of the reconstructed images in the Z=0 plane using 4,902 transducers and the corresponding absolute error images. The absolute error image is derived by subtracting the reconstructed conductivity image from the target image and taking the absolute value. FIG. 16(a) suggests that the MAT-MI can reconstruct the image with low contrast, as in the case of 0.25 S/m inner layer conductivity vs 0.2 S/m background conductivity. In addition, it is shown that the reconstruction error is focused on the conductivity boundary areas. This kind of error is due to the boundary shift introduced by use of the median filter. FIGS. 16(b) and 16(c) show the corresponding CC and RE. The mean reconstructed conductivity in each layer and related average conductivity error is presented in Table I. In the estimation of the mean reconstructed conductivity and ACE, the large boundary errors shown in FIG. 16(a) are excluded. The inner layer area refers to the spherical region of r<26 mm, the outer layer refers to the region 30 mm≤r<56 mm. From Table I, shown in FIG. 20, the average conductivity error is no more than 5% for each case, indicating the accuracy of the MAT-MI reconstruction.

Figure 17A:
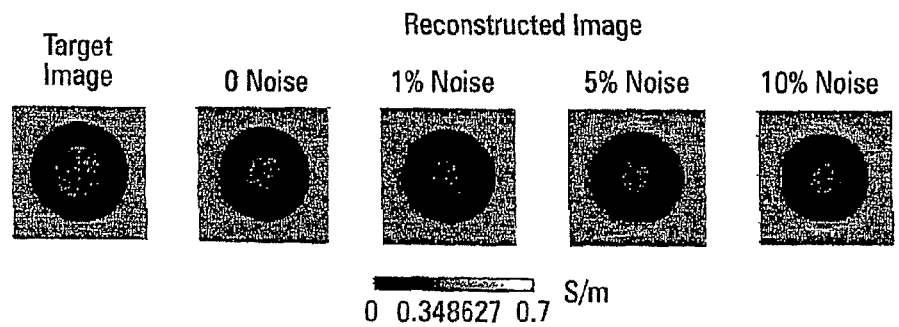
FIGS. 17(a), 17(b), and 17(c) illustrate target and reconstructed images, correlation coefficients, and relative error, respectively.

Finally, the influence of noise on the MAT-MI reconstruction is investigated and shown in FIG. 17. In this simulation, the conductivity values $\sigma_1$, $\sigma_2$ and $\sigma_3$ were set to 0.25, 0.04 and 0.4 S/m respectively and $r_1$ was set to 30 mm. Zero mean Gaussian white noise was added to the pressure signal to simulate noise-contaminated transducer measurements. The noise standard deviation was set to be the product of the noise level and the root mean square (rms) of all the noise-free pressure measurements, FIG. 17 shows the reconstructed images using 4,902 transducers under different noise levels.

Figure 17B:
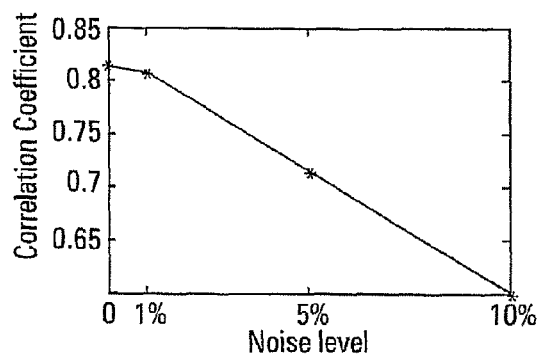
Figure 17C:
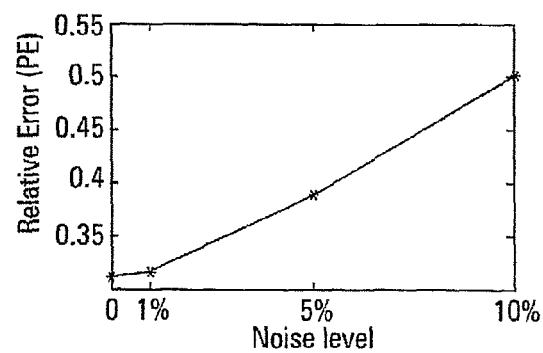

Corresponding CC and RE of this reconstruction are also shown in FIG. 17. Both CC and RE, as shown in FIG. 17(b)-(c), are sensitive to the noise level in that 10% noise would cause a 0.21 decrease in CC and a 0.19 increase in RE, as compared with the noise-free reconstruction.

Magnetic Resonance Electrical Impedance Tomography with Magnetic Induction

Figure 18:
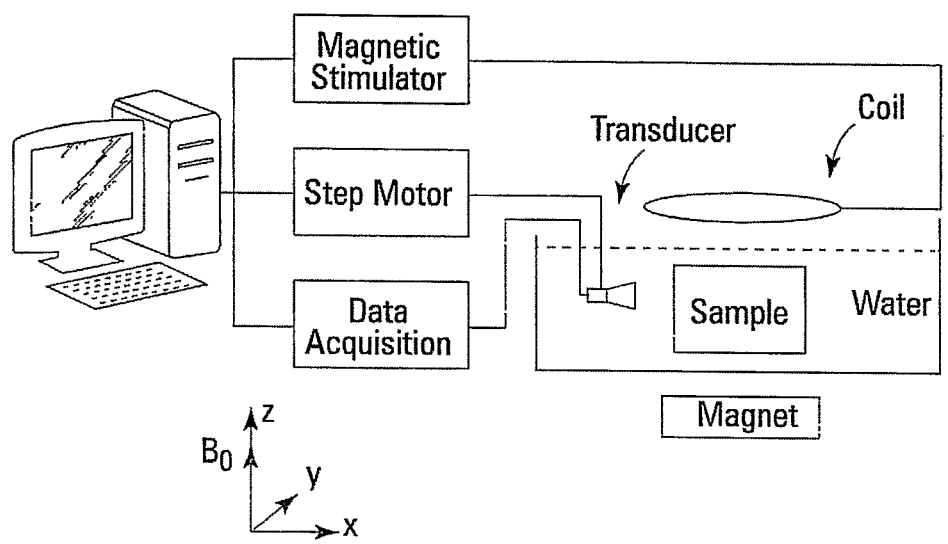
FIG. 18 illustrates a method for determining a conductivity distribution in a subject in accordance with some embodiments.

FIG. 18 illustrates a method for determining a conductivity distribution in a subject in accordance with some embodiments. A 3-D model of a body or sample is constructed from a MRI of a subject. Magnetic stimulation is used to induce current density within the body through one or multiple pairs of coils with pulsed steady frequency signals. An MRI scanner measure one or multiple components of the induced magnetic flux density distribution due to magnetic stimulation. The forward solver computes the magnetic flux density distribution using an assumed conductivity distribution within the body. The measured and model-computed magnetic flux density distribution is compared and the difference evaluated. If the difference is not smaller than a threshold value, then the conductivity profile of the body is revised and the forward computation retaken, until the difference between the measured and model-predicted magnetic flux density distribution is smaller than the threshold value. The conductivity distribution of the body is reconstructed when the procedure converges, and displayed in a displaying device.

According to another embodiment, the electrical current density distribution within a body is imaged. A 3-D model of the body is constructed from an MRI of a subject. Magnetic stimulation is used to induce current density within the body through one or multiple pairs of coils with pulsed or steady frequency signals. An MRI scanner measures multiple components of the induced magnetic flux density. The current density distribution is derived from the measured magnetic flux density distribution.

According to another embodiment, a 3-D model of the body is constructed from an MRI of a subject. Magnetic stimulation is used to induce current density within the body through one or multiple pairs of coils with pulsed or steady frequency signals. An MRI scanner measures one or multiple components of the induced magnetic flux density, and derives the current density distribution within the body. The forward solver computes the current density distribution using the assumed conductivity distribution within the body. The measured and model-computed current density distribution is compared and the difference evaluated. If the difference is not smaller than a threshold value, then the conductivity profile of the body is revised and forward computation retaken, until the difference between the measured and model-predicted current density distribution is smaller than the threshold value. The conductivity distribution of the body is reconstructed when the procedure converges, and displayed in a displaying device.

According to one embodiment, the body may be represented by a piecewise homogeneous model, in which only the discrete values of conductivity profiles for each of the homogenous region is estimated. Such piecewise homogeneous model has wide applications in bioelectromagnetic forward and inverse problems from body surface electrical recordings or biomagnetic recordings out of the body. The boundary element method is used to solve the forward problem in this embodiment.

According to another embodiment, the body is represented by an isotropic inhomogeneous model, in which a continuous distribution of conductivity profiles is estimated. The finite element method or finite difference method or other numerical methods can be used to solve the forward problem in this embodiment.

According to another embodiment, the body maybe presented by an anisotropic inhomogeneous model, in which continuous distribution of tissue may be estimated by using diffusion tensor magnetic resonance imaging, and finite element method or finite difference method can be used to solve the forward problem in this embodiment.

According to another embodiment, the difference between the measured and model-predicted signals is considered as the L2 norm, L1 norm, or other norms.

According to another embodiment, the minimization of the difference between the measured and model-predicted signals is realized by using an automatic searching algorithm or an artificial neural network based algorithm.

According to yet another embodiment, the impedance distribution of the body is reconstructed by the above procedures, and the impedance information is used to detect cancers, stroke, myocardial infarction, ischemia; or used to aid source localization in epilepsy patients from an electroencephalogram (EEG) or magnetoencephalogram (MEG), aiding surgical or presurgical planning; or used to aid in cardiac source imaging to assist in catheter ablation in arrhythmia patients.

Figures 19A, 19B:
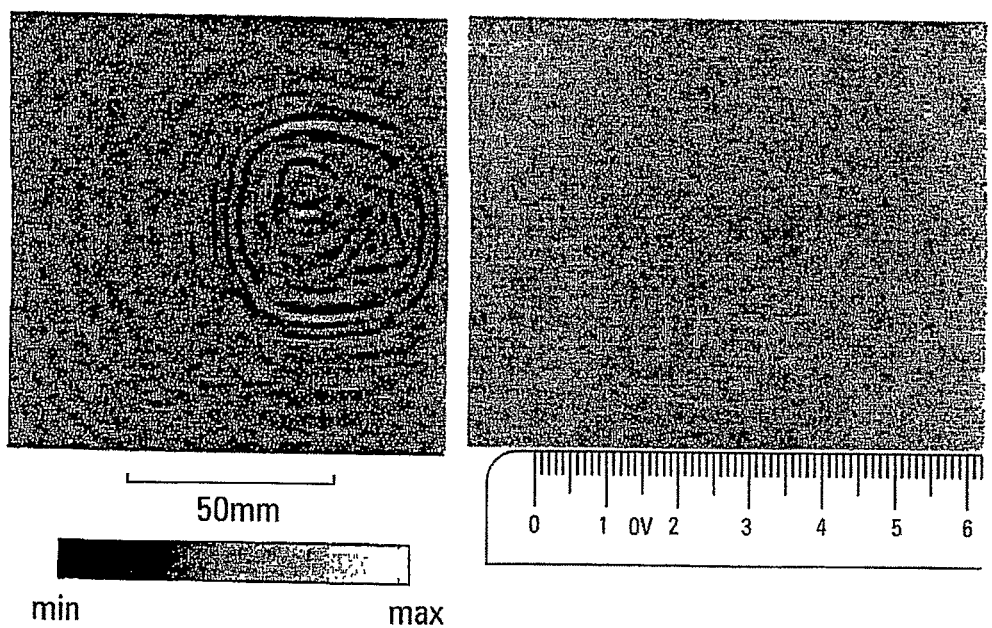
FIG. 19 is a block diagram of an apparatus including an imaging system, a model of an object to be imaged, a stimulation system, and a computation unit in accordance with some embodiments.

FIG. 19 is a block diagram of an apparatus 2200 including an imaging system 2202, a model 2204 of an object to be imaged, a stimulation system 2206, and a computation unit 2208 in accordance with some embodiments. The imaging system 2202 is coupled to the computation unit 2208. The computation unit 2208 is coupled to the model 2204. The stimulation system 2206 provides a stimulation signal 2210 to an object 2212. The imaging system 2202 receives a signal 2214 from the object 2212. In some embodiments, the object 2212 includes biological materials. In other embodiments, the object 2212 includes non-biological materials.

The imaging system 2202 is not limited to a particular type of imaging system. In some embodiments, the imaging system 2202 includes a magnetic resonance imaging system. In some embodiments, the current density in the object 2212 is imaged. In other embodiments, magnetic flux density or components of magnetic flux in the object 2212 is imaged. In other embodiments, electrical impedance in the object 2212 is imaged.

Exemplary models 2204 suitable for use in connection with the apparatus 2200 include homogeneous models, isotropic inhomogeneous models, and anisotropic inhomogeneous models.

The stimulation system 2206 provides the stimulation signal 2210 to the object 2212. Induced signals in the object 2212 are imaged by the imaging system 2202. In some embodiments, the stimulation system 206 induces currents in the object 2212 through magnetic induction. In other embodiments, the stimulation system 206 induces magnetic signals in the object 2212 through acoustic stimulation.

The computation unit 2208 includes an algorithm to decrease the difference between a measured signal 2216 and a model predicted signal 2218. Exemplary computation units suitable for use in connection with the apparatus 2200 include artificial neural networks and automatic searching algorithms.

In operation, the stimulation system 2206 provides the stimulation signal 2210 to the object 2212. The signal 2214 is induced in the object 2212 by the stimulation signal 2210. The imaging system 2202 receives the signal 2214 from the object 2212. The computation unit 2208 receives the measured signal 2216 from the imaging system 2202 and the modeled predicted signal 2218 from the model 2204. The computation unit 2208 reduces the difference between the measured signal 2216 received from the imaging system 2202 and the model predicted signal 2218.

What is claimed is:

1. An apparatus comprising:
a magnetic energy source configured to provide a static magnetic field oriented along a direction and a magnetic signal that induces electrical currents in a sample, the magnetic signal being oriented along the same direction as the static magnetic field;
a detector configured to detect an acoustic energy signal that is produced in response to forces generated by a combination of the induced electrical currents and the static magnetic field; and
a computer to process the acoustic energy signal to:
determine an electrical impedance distribution of the sample;
produce an electrical impedance image that depicts the determined electrical impedance distribution of the sample;
display the electrical impedance image in a displaying device, in conjunction with other anatomic imaging results; and
identify cancer from impedance contrast in the electrical impedance distribution of the sample.

2. The apparatus of claim 1, wherein the magnetic signal includes a non-static magnetic signal.

3. The apparatus of claim 2, wherein the non-static magnetic signal includes a pulsed magnetic signal.

4. A method comprising:
positioning a sample in a static magnetic field that is oriented along a direction;
applying a magnetic signal to the sample to induce electrical currents in the sample, the magnetic signal being applied in the same direction along which the static magnetic field is oriented;
detecting an acoustic signal from the sample that is formed in response to forces generated in the sample by a combination of the induced electrical currents and the static magnetic field;
processing the acoustic signal to form an image of an electrical property distribution in the sample; and
displaying the electrical property image in a displaying device, in conjunction with other anatomic imaging results; and
identifying cancer from a contrast in the image of the electrical property distribution in the sample.

5. The method of claim 4, wherein applying a magnetic signal to a sample includes applying a non-static magnetic field to the sample.

6. The method of claim 4, wherein the electrical property distribution is an electrical impedance distribution and processing the acoustic signal to form the image of the electrical property distribution in the sample includes processing the acoustic signal to determine the electrical impedance distribution in the sample and forming the image as an image that depicts the determined electrical impedance distribution in the sample.

7. The method of claim 4, wherein the electrical property distribution is an eddy current distribution and processing the acoustic signal to form the image of the electrical property distribution in the sample includes processing the acoustic signal to determine the eddy current distribution in the sample and forming the image as an image that depicts the determined eddy current distribution in the sample.

8. A method comprising:
positioning a biological sample in a static magnetic field that is oriented along a direction;
applying a magnetic signal to the biological sample to induce electrical currents in the biological sample, the magnetic signal being applied in the same direction along which the static magnetic field is oriented;
detecting an acoustic signal from the biological sample that is formed in response to forces generated in the biological sample by a combination of the induced electrical currents and the static magnetic field;
processing the acoustic signal to determine an electrical impedance distribution of the biological sample;
producing an electrical impedance image that depicts the determined electrical impedance distribution of the biological sample; and
identifying disease from impedance contrast in the electrical impedance distribution of the biological sample.

9. A method comprising,
positioning a biological sample in a static magnetic field that is oriented along a direction;
applying a magnetic signal to the biological sample to induce electrical currents in the biological sample, the magnetic signal being applied in the same direction along which the static magnetic field is oriented;
detecting an acoustic signal from the biological sample; that is formed in response to forces generated in the biological sample by a combination of the induced electrical currents and the static magnetic field; and
processing the acoustic signal to determine an electrical impedance distribution of the biological sample;
producing an electrical impedance image that depicts the determined electrical impedance distribution of the biological sample; and
displaying the electrical impedance image in a displaying device, in conjunction with other anatomic imaging results to aid detecting and diagnosing of cancer based on an impedance contrast in the electrical impedance distribution of the biological sample.

10. A method comprising:
positioning a biological sample in a static magnetic field that is oriented along a direction;
applying a magnetic signal to the biological sample to induce electrical currents in the biological sample, the magnetic signal being applied in the same direction along which the static magnetic field is oriented;
detecting an acoustic signal from the biological sample that is formed in response to forces generated in the biological sample by a combination of the induced electrical currents and the static magnetic field;
processing the acoustic signal to determine an electrical impedance distribution of the biological sample;
producing an electrical impedance image that depicts the determined electrical impedance distribution of the biological sample; and
displaying the electrical impedance image in a displaying device, in conjunction with other anatomic imaging results for applications in arrhythmia management.

11. A method comprising:
positioning a neurological sample in a static magnetic field that is oriented along a direction;
applying a magnetic signal to the neurological sample to induce electrical currents in the neurological sample, the magnetic signal being applied in the same direction along which the static magnetic field is oriented;
detecting an acoustic signal from the neurological sample that is formed in response to forces generated in the neurological sample by a combination of the induced electrical currents and the static magnetic field;
processing the acoustic signal to determine an electrical impedance distribution of the biological sample;
producing an electrical impedance image that depicts the determined electrical impedance distribution of the biological sample; and
displaying the electrical impedance image in a displaying device, in conjunction with other anatomic imaging results to determine functions and dysfunctions in the neurological sample based on an impedance contrast in the electrical impedance distribution of the biological sample.

12. A method comprising:
positioning a sample in a static magnetic field;
applying a magnetic signal to the sample to induce electrical currents in the sample;
detecting an acoustic signal from the sample that is formed in response to forces generated in the sample by a combination of the induced electrical currents and the static magnetic field;
processing the acoustic signal to determine an electrical impedance distribution of the sample;
producing an electrical impedance image that depicts the determined electrical impedance distribution of the sample;
displaying the electrical impedance image in a displaying device, in conjunction with other anatomic imaging results; and
identifying cancer from impedance contrast in the electrical impedance distribution of the sample.

13. An apparatus comprising:
a magnetic energy source to provide:
 a static magnetic field that is oriented along a direction; and
 a magnetic signal that is oriented along the same direction as the static magnetic field and that induces electrical currents in a sample including human breast tissue;
a detector to detect an acoustic energy signal that is produced in response to forces generated by a combination of the induced electrical currents and the static magnetic field; and
a computer to process the acoustic energy signal to:
 determine an electrical impedance distribution in the human breast tissue;
 produce an electrical impedance image that depicts the determined electrical impedance distribution in the human breast tissue, and
 identify cancer from impedance contrast in the electrical impedance distribution of the human breast tissue.

14. A method comprising:
positioning a sample in a static magnetic field that is oriented along a direction;
applying a magnetic signal to the sample to induce electrical currents in the sample, the magnetic signal being applied in the same direction along which the static magnetic field is oriented;
detecting an acoustic signal from the sample that is formed in response to forces generated in the sample by a combination of the induced electrical currents and the static magnetic field;
processing the acoustic signal to derive a current density distribution for the sample;
producing a current density image that depicts the current density distribution for the sample; and
displaying the current density image in a displaying device in conjunction with other anatomic imaging results, to aid detecting and diagnosing of cancer.

15. A method comprising:
positioning a sample in a static magnetic field that is oriented along a direction;
applying a magnetic signal to the sample to induce electrical currents in the sample, the magnetic signal being applied in the same direction along which the static magnetic field is oriented;
detecting an acoustic signal from the sample that is formed in response to forces generated in the sample by a combination of the induced electrical currents and the static magnetic field;
processing the acoustic signal to derive a conductivity value for the sample;
producing an conductivity image that depicts the conductivity value for the sample; and
displaying the conductivity image in a displaying device, in conjunction with other anatomic imaging results, to aid detecting and diagnosing of cancer.

16. A method comprising:
positioning a sample in a static magnetic field that is oriented along a direction;
applying a magnetic signal to the sample to induce electrical currents in the sample, the magnetic signal being applied in the same direction along which the static magnetic field is oriented;
detecting an acoustic signal from the sample that is formed in response to forces generated in the sample by a combination of the induced electrical currents and the static magnetic field;
processing the acoustic signal to identify one or more locations of conductivity change in the sample;
producing an image that depicts the one or more locations of conductivity change in the sample; and
displaying the image in a displaying device, in conjunction with other anatomic imaging results, to aid detecting and diagnosing of cancer.

17. A method comprising:
positioning a sample in a static magnetic field;
applying a magnetic signal to the sample to induce electrical currents in the sample;
detecting an acoustic signal from the sample that is formed in response to forces generated in the sample by a combination of the induced electrical currents and the static magnetic field; and
processing the acoustic signal to determine an eddy current distribution in the sample;
processing the acoustic signal to determine a combined current distribution in the sample, the combined current distribution representing the eddy current distribution in the sample and a biological current distribution in the sample; and
subtracting the eddy current distribution from the combined current distribution to determine the biological current distribution in the sample.

* * * * *